(12) United States Patent
Wang et al.

(10) Patent No.: US 12,064,447 B1
(45) Date of Patent: Aug. 20, 2024

(54) LYOPHYLLUM DECASTES POLYSACCHARIDE, PREPARATION METHOD AND APPLICATION THEREOF

(71) Applicant: Jilin Agricultural University, Jilin (CN)

(72) Inventors: Qi Wang, Jilin (CN); Ling Su, Jilin (CN); Yan Zhang, Jilin (CN); Yu Li, Jilin (CN); Min Gao, Jilin (CN); Xueyu Shang, Jilin (CN); Tianci Wang, Jilin (CN)

(73) Assignee: Jilin Agricultural University, Jilin (CN)

( * ) Notice: Subject to any disclaimer, the term of this patent is extended or adjusted under 35 U.S.C. 154(b) by 0 days.

(21) Appl. No.: 18/399,599

(22) Filed: Dec. 28, 2023

Related U.S. Application Data

(63) Continuation of application No. PCT/CN2023/131160, filed on Nov. 13, 2023.

(30) Foreign Application Priority Data

Mar. 10, 2023 (CN) .......................... 202310226009.3

(51) Int. Cl.
*A61K 31/715* (2006.01)
*A61P 1/00* (2006.01)
*A61P 29/00* (2006.01)
*A61P 39/06* (2006.01)

(52) U.S. Cl.
CPC ............. *A61K 31/715* (2013.01); *A61P 1/00* (2018.01); *A61P 29/00* (2018.01); *A61P 39/06* (2018.01)

(58) Field of Classification Search
None
See application file for complete search history.

(56) References Cited

FOREIGN PATENT DOCUMENTS

| | | | | |
|---|---|---|---|---|
| CN | 104017103 | A | | 9/2014 |
| CN | 107663244 | A | * | 2/2018 ......... C08B 37/0003 |
| CN | 107663244 | A | | 2/2018 |
| CN | 107936141 | A | | 4/2018 |
| CN | 108840960 | A | * | 11/2018 ......... C08B 37/0003 |
| CN | 110218264 | A | * | 9/2019 ........... A23L 33/125 |

OTHER PUBLICATIONS

Liu, J., Wu, L., Li, N., Chen, Z., & Lan, Q. (Dec. 2019). Optimization of extraction method for extracellular polymeric substances of Phanerochaete chrysosporium. In IOP Conference Series: Earth and Environmental Science (vol. 371, No. 4, p. 042008). IOP Publishing. (Year: 2019).*
Wang, W., Liu, W., & Wang, L. (2015). Comparative Research on EPS Extraction from Mechanical Dewatered Sludge with Different Methods. International Journal Bioautomation, 19(3), 409-418. (Year: 2015).*
Dou Yong et al., "Extracting chitin in freshwater crayfish shell with ultrasonic assisted EDTA method," Guangdong Agricultural Sciences, Nov. 2014, 22.
First Office Action for China Application No. 202310226009.3, mailed Sep. 7, 2023.
Gao Huijuan et al., "Optimization of extraction technology and infrared spectrum analysis of selenium polysaccharide from the mycelium of selenium-enriched Lyophyllum decastes," Food and Fermentation Industries, Jan. 2018, pp. 151-158, vol. 44, No. 3.
Wang Xiao-Qin et al., "Study on Extraction Technology and Antifungal Action of Lyophyllum Decastes Polysaccharide," CFI, Dec. 2009, 12.
Zhang Chun-Mei et al., "Study on the Extraction and Ferric Reducing Antioxidant Power of Polysaccharide of Lyophyllum decastes," Edible Fungi of China, Sep. 2012, pp. 44-48, 31.
Zhou Zhiqiang et al., "The Preparation and Biological Activity of Selenium-Enriched Lyophyllum decastes Mycelium," Food industry, May 2019, pp. 228-231.
Notification to Grant Patent for China Application No. 202310226009. 3, mailed Sep. 21, 2023.
First Search Report for China Application No. 202310226009.3, dated Sep. 6, 2023.
Supplementary Search Report for China Application No. 202310226009. 3, dated Sep. 18, 2023.

* cited by examiner

*Primary Examiner* — Dale R Miller

(74) *Attorney, Agent, or Firm* — Pilloff Passino & Cosenza LLP; Rachel K. Pilloff; Sean A. Passino

(57) ABSTRACT

A *Lyophyllum decastes* polysaccharide, a preparation method and an application thereof are provided in the present disclosure, relating to the technical field of biomedicine. The preparation method includes the following steps: (1) adding an aqueous solution containing EDTA-2Na into a fruiting body of *Lyophyllum decastes*, performing ultrasonic treatment, and then performing water extraction treatment to obtain an extractive solution; (2) concentrating the extractive solution, adding anhydrous ethanol for precipitation, followed by centrifuging to obtain precipitates, then obtaining a crude *Lyophyllum decastes* polysaccharide; and (3) conducting removal of proteins and dialysis of the crude *Lyophyllum decastes* polysaccharide to obtain the *Lyophyllum decastes* polysaccharide.

1 Claim, 27 Drawing Sheets

LYOPHYLLUM DECASTES POLYSACCHARIDE, PREPARATION METHOD AND APPLICATION THEREOF

CROSS-REFERENCE TO RELATED APPLICATIONS

This application is a continuation of PCT/CN2023/131160, filed on Nov. 13, 2023, and claims priority of Chinese Patent Application No. 202310226009.3, filed on Mar. 10, 2023, the entire contents of which are incorporated herein by reference.

TECHNICAL FIELD

The present disclosure relates to the technical field of biomedicine, and in particular to a *Lyophyllum decastes* polysaccharide, a preparation method and an application thereof.

BACKGROUND

Along with the progress and development of life science and technology, both surgical treatment and drug treatment of cancer have achieved remarkable results, especially drug treatment, with the exception that long-term administration will cause damage to the immune system of the organism and induce a series of adverse reactions. Studies have found that plant polysaccharides are effective in treating the adverse reactions caused by anticancer drugs, providing a new way of the protection and treatment of the adverse reactions caused by anticancer drugs. *Lyophyllum decastes* (formal name of *Lyophyllum decastes* (Fr.:Fr.)Sing.) is a large and valuable wild fungus, with delicious flesh, rich nutritional value, as well as various pharmacological activities such as antioxidant, anti-tumour, and so on, making it of high value for health care and medicinal development. Nevertheless, the research on the *Lyophyllum decastes* at this stage mainly focuses on artificial cultivation and domestication, nutrients research and extraction methods, etc., with less research in the immunomodulation-related aspects, and the bioactivity and research methods of regulating intestinal immunocompromise caused by antitumour drugs have not been reported yet.

SUMMARY

It is an objective of the present disclosure to provide a *Lyophyllum decastes* polysaccharide, a preparation method and an application thereof, so as to solve the problems existing in the prior art. The *Lyophyllum decastes* polysaccharide prepared by the present disclosure has the function of alleviating intestinal immunocompromise.

In order to achieve the above objective, the present disclosure provides the following technical scheme.

The present disclosure provides a preparation method of a *Lyophyllum decastes* polysaccharide, including following steps:

S1, adding an aqueous solution containing EDTA-2Na (disodium ethylene diamine tetraacetate) into a fruiting body of *Lyophyllum decastes*, performing ultrasonic treatment, and then performing water extraction treatment to obtain an extractive solution;

S2, concentrating the extractive solution, adding anhydrous ethanol for precipitation, followed by centrifuging to obtain precipitates as a crude *Lyophyllum decastes* polysaccharide; and S3, conducting removal of proteins and dialysis of the crude *Lyophyllum decastes* polysaccharide to obtain the *Lyophyllum decastes* polysaccharide.

Optionally, in the S1, a concentration of the EDTA-2Na in the aqueous solution containing EDTA-2Na is 1 weight percentage (wt %).

Optionally, in the S1, a material-liquid ratio of the fruiting body of the *Lyophyllum decastes* to the aqueous solution containing EDTA-2Na is 1 gram (g): 22 milliliters (mL).

Optionally, in the S1, a duration of the ultrasonic treatment is 30 minutes (min).

Optionally, in the S1, a power of the ultrasonic treatment is 100 watts (W).

Optionally, in the S1, a duration of the water extraction treatment is 3 hours (h).

Optionally, in the S1, a temperature of the water extraction treatment is 98 degrees Celsius (° C.).

The present disclosure also provides a *Lyophyllum decastes* polysaccharide prepared by the preparation method.

The present disclosure also provides an application of the *Lyophyllum decastes* polysaccharide in preparing medicines for alleviating intestinal immunocompromise.

Optionally, the intestinal immunocompromise is caused by anti-tumor drugs.

The present disclosure achieves the following technical effects.

In the present disclosure, EDTA-2Na-assisted ultrasonic method is adopted to extract and obtain the *Lyophyllum decastes* polysaccharide; under the cavitation effect, mechanical effect and thermal effect of ultrasonic wave, polysaccharide molecules in the cell wall of *Lyophyllum decastes* are accelerated to release and diffuse, and the dissolution rate of polysaccharide is therefore improved; EDTA-2Na is an ammonia-carboxylate complexing agent with properties of antioxidant, increasing stability and softening; by adding a certain amount of EDTA-2Na in the extraction of the *Lyophyllum decastes* polysaccharide, the metal ions in water are chelated, the polysaccharides aggregated by the chemical bonds of the metal ions are disrupted, therefore increasing the solubility of the polysaccharides, lowering the molecular weight of the polysaccharides, preventing metal-induced discolouration, deterioration, etc., and thus improving the purity of the polysaccharides; the polysaccharide extracted by the present disclosure has a sugar content of 75.47 wt %, a protein content of 5.78 wt % and a uronic acid content of 8.85 wt %, and includes seven monosaccharides, namely mannose, ribose, glucuronic acid, glucose, galactose, xylose and fucose, with glucose and galactose as the main components and a certain amount of mannose, ribose, glucuronic acid, fucose and a small amount of xylose; the average molecular weight, peak molecular weight, weight-average molecular weight and number-average molecular weight of the polysaccharide are 51868 grams per mole (g/mol), 50799 g/mol, 51770 g/mol and 51680 g/mol, respectively.

The purified polysaccharide may also undergo some changes in aspects of physics, chemistry and function in the process of preparation, especially the differences in monosaccharides and molecular weight, which may result in the loss or generation of various biological activities; through the research on the pharmacological activities of the *Lyophyllum decastes* polysaccharide extracted in the present disclosure, it is found that the polysaccharide has the function of regulating the intestinal immune function of immunocompromised mice, including increasing the weight and spleen and thymus indexes, enhancing the antioxidant effect of immune organs, and reducing the level of inflammation, repairing the colon tissue damage, improving the diversity of intestinal microbial community, adjusting the structure and composition of microbial community.

BRIEF DESCRIPTION OF THE DRAWINGS

For a clearer description of the technical schemes in the embodiments or prior art of the present disclosure, the accompanying drawings to be used in the embodiments are briefly described hereinafter, and it is obvious that the accompanying drawings in the description hereinafter are only some of the embodiments of the present disclosure, and that for the person of ordinary skill in the field, other accompanying drawings are available on the basis of the accompanying drawings without any creative labour.

DETAILED DESCRIPTION OF THE EMBODIMENTS

Various exemplary embodiments of the present disclosure are now described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges can be independently included or excluded from the range.

Unless otherwise specified, all technical and scientific terms used herein have the same meaning as commonly understood by one of ordinary skill in the art to which this present disclosure relates. Although the present disclosure only describes the preferred methods and materials, any methods and materials similar or equivalent to those described herein can also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes can be made to the specific embodiments of the present disclosure without departing from the scope or spirit of the present disclosure. Other embodiments will be apparent to the skilled person from the description of the present disclosure. The description and embodiments of that present disclosure are exemplary only.

The terms "including", "comprising", "having" and "containing" used in this specification are all open terms, which means including but not limited to.

*Lyophyllum decastes* used in the following embodiments are provided by Guizhou Jianrong Biotechnology Co., Ltd.

Figure 16:
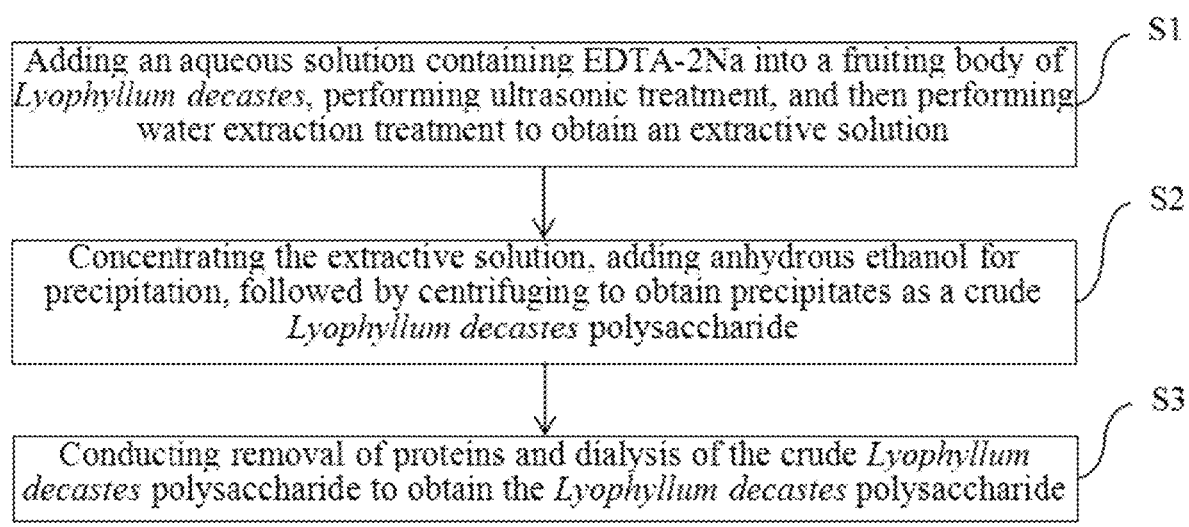
FIG. 16 is a process illustrating a preparation method of the *Lyophyllum decastes* polysaccharide provided by the present disclosure.

The present disclosure provides a preparation method of a *Lyophyllum decastes* polysaccharide, including following steps as shown in FIG. 16:

S1, adding an aqueous solution containing EDTA-2Na (disodium ethylene diamine tetraacetate) into a fruiting body of *Lyophyllum decastes*, performing ultrasonic treatment, and then performing water extraction treatment to obtain an extractive solution;

S2, concentrating the extractive solution, adding anhydrous ethanol for precipitation, followed by centrifuging to obtain precipitates as a crude *Lyophyllum decastes* polysaccharide; and S3, conducting removal of proteins and dialysis of the crude *Lyophyllum decastes* polysaccharide to obtain the *Lyophyllum decastes* polysaccharide.

Embodiment 1

1. Methods 1.1 Single Factor 1.1.1 Effect of Material-Liquid Ratio on Polysaccharide Content of *Lyophyllum decastes*

5 parts of *Lyophyllum decastes* which have been dried and crushed and sieved by a 40-mesh sieve are weighed, each of 5 grams (g) and are added with 2 weight percentage (wt %) of EDTA-2Na (disodium ethylene diamine tetraacetate) aqueous solution according to the material-liquid ratio of 1:10, 1:20, 1:30, 1:40 and 1:50 g/mL respectively, followed by room temperature soaking for 2 hours (h), then subjecting to ultrasonic treatment at 100 watts (W) for 30 minutes (min), and extraction for 3 h with extraction temperature set at 98 degrees Celsius (° C.); the extraction is repeated once under the same conditions, and the two extractive solutions are combined, concentrated, precipitated by adding 3 times the volume of anhydrous ethanol, stood at 4° C. overnight and then centrifuged at 4000 revolutions per minutes (rpm) for 10 min to collect the precipitate as the crude *Lyophyllum decastes* polysaccharide, followed by subjecting to removal of proteins and dialysis, then the lyophilisation is carried out to obtain the *Lyophyllum decastes* polysaccharides to determine the effect of different extraction durations on the polysaccharide content.

1.1.2 Effect of Extraction Duration on Content of *Lyophyllum decastes* Polysaccharide 5 parts of *Lyophyllum decastes* which have been dried and crushed and sieved by a 40-mesh sieve are weighed, each of 5 g and are added with 2 wt % of EDTA-2Na aqueous solution according to the material-liquid ratio of 1:30 g/mL, followed by room temperature soaking for 2 h, then subjecting to ultrasonic treatment at 100 W for 30 min, and extraction for 1, 2, 3, 4, and 5 h respectively with extraction temperature set at 98° C.; the extraction is repeated once under the same conditions, and the two extractive solutions are combined, concentrated, precipitated by adding 3 times the volume of anhydrous ethanol, and centrifuged at 4000 rpm for 10 min at 4° C. overnight to collect the precipitate to obtain the crude *Lyophyllum decastes* polysaccharide, followed by subjecting to removal of proteins and dialysis, then the lyophilisation is carried out to obtain the polysaccharides of the *Lyophyllum decastes* to determine the effect of different extraction durations on the polysaccharide content.

1.1.3 Effect of EDTA-2Na Concentration on the Content of *Lyophyllum decastes* Polysaccharide 5 parts of *Lyophyllum decastes* which have been dried and crushed and sieved by a 40-mesh sieve are weighed, each of 5 g and are added with 0.5, 1.0, 1.5, 2.0 and 2.5 wt % of EDTA-2Na aqueous solution respectively according to the material-liquid ratio of 1:30 g/mL, followed by room temperature soaking for 2 h, then subjecting to ultrasonic treatment at 100 W for 30 min, and extraction for 3 h with extraction temperature set at 98° C.; the extraction is repeated once under the same conditions, and the two extractive solutions are combined, concentrated, precipitated by adding 3 times the volume of anhydrous ethanol, and centrifuged at 4000 rpm for 10 min at 4° C. overnight to collect the precipitate as the crude *Lyophyllum decastes* polysaccharide, followed by subjecting to removal of proteins and dialysis, then the lyophilisation is carried out to obtain the *Lyophyllum decastes* polysaccharide to determine the effect of different concentrations of EDTA-2Na on the polysaccharide content.

1.2 Optimization of Extraction Process of *Lyophyllum decastes* Polysaccharide by Response Surface Methodology Box-Behnken method is used to optimize the extraction technology of *Lyophyllum decastes* polysaccharide. According to the results of single factor tests, the response surface optimization experiment is carried out with the content of *Lyophyllum decastes* polysaccharide as the response value, and the material-liquid ratio (A), extraction duration (B) and EDTA-2Na concentration (C) as the independent variables. A mathematical model is developed through multiple regression analysis to determine the optimal extraction conditions and to study the relationship between the response variables and the experimental variables, as shown in Table 1.

TABLE 1

Box-Behnken experimental factors and levels

| Levels | Material-liquid ratio (g/mL) A | Time (h) B | EDTA-2Na concentration (wt %) C |
|---|---|---|---|
| −1 | 1:20 | 2 | 0.5 |
| 0 | 1:30 | 3 | 1 |
| 1 | 1:40 | 4 | 1.5 |

1.3 Extraction Process of *Lyophyllum decastes* Polysaccharide (1) Extraction: according to the optimal process determined in sections 1.1 and 1.2, the crude *Lyophyllum decastes* polysaccharide is extracted.

(2) Impurity removal and refining: protein is removed by sevag method; polysaccharide solution: sevag reagent (mixture of chloroform and n-butanol in 4:1)=1:2, followed by stirring by magnetic stirrer for 30 min, and resting for stratification; the upper organic reagent layer and the middle milky white protein layer are discarded, and the lower layer of polysaccharide is collected and continued to be added with sevag reagent proportionally, and the above operations are repeated for three times; then, the dialysis bag with molecular weight cut-off of 3500 Da is used to dialyze the protein-free *Lyophyllum decastes* polysaccharide for 1 day, followed by dialyzing with pure water for 1 day, and then freeze-drying, and finally the *Lyophyllum decastes* polysaccharide is obtained, named LDP.

1.4 Detection Methods

Phenol-sulfuric acid method is used to determine the total sugar content of *Lyophyllum decastes* polysaccharide. The content of reducing sugar in *Lyophyllum decastes* polysaccharide is measured by the 3,5-dinitrosalicylic (DNS) acid method; and the content of uronic acid in *Lyophyllum decastes* polysaccharide is determined by m-hydroxybiphenyl method.

High performance liquid chromatography (HPLC) is used to analyze the monosaccharide composition in the *Lyophyllum decastes* polysaccharide, with detection conditions as follows:
(1) the data acquisition instrument system includes Agilent 1200, and the detector is ultraviolet detector;
(2) chromatographic column: C18 Agilent 4.6 mm*250 mm*5 μm;
(3) mobile phase A: 0.1 mol/L 0.1 M $KH_2PO_4$ (pH 6.8); mobile phase B: acetonitrile;
(4) gradient of the mobile phases: A:B=82:18, isocratic elution;
(5) flow rate: 1.0 mL/min; column temperature: 25° C.; sample volume: 10 μL; detection wavelength: 245 nm.

The purity and molecular weight of the components of the *Lyophyllum decastes* polysaccharide e determined by Gel Permeation Chromatography/Size-Exclusion Chromatography (GPC/SEC) system with 1260 Infinity II multi-detectors, and the detection conditions are as follows:
(1) chromatographic column: PL aquagel-OH Mixed-H, 8 μm, 7.5×300 mm (molecular weight range of 200-10000000);
(2) detectors: differential detector, double-angle laser scattering detector and viscosity detector;
(3) flow rate: 1.0 mL/min, column temperature: 45° C.; sample volume: 50 μL;
(4) mobile phase: 0.1 mol/L sodium nitrate (0.01% sodium azide), isocratic elution.

Using potassium bromide (KBr) tabletting method, the infrared spectrum analysis of *Lyophyllum decastes* polysaccharide is carried out, including: accurately weighing 2 mg of *Lyophyllum decastes* polysaccharide, grinding it together with chromatographic pure KBr in agate mortar, fully mixing it, and tabletting it into thin slices with tabletting machine, adjusting the Fourier infrared spectrometer in the frequency range of 4000-500 $cm^{-1}$, and scanning and analyzing the infrared spectrum, repeating the detection for 3 times to obtain an average spectrum.

2. Results

2.1 Optimization of Extraction Process of *Lyophyllum decastes* Polysaccharide

2.1.1 Single Factor Test Results

Figure 1:
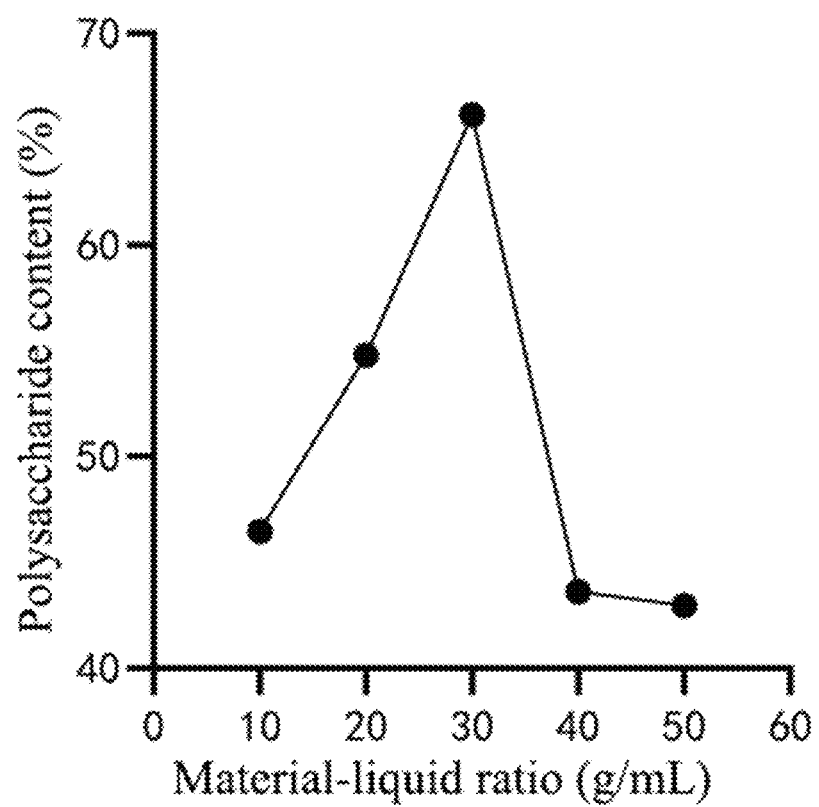
FIG. 1 shows the effect of the material-liquid ratio on the polysaccharide content.

2.1.1.1 Effect of Material-Liquid Ratio on *Lyophyllum decastes* Polysaccharide Content As shown in FIG. 1, the content of *Lyophyllum decastes* polysaccharide increases with the increasing of the material-liquid ratio when the material-liquid ratio is in the range of 1:10-1:30 g/mL, while it decreases with the continuous increase of the material-liquid ratio when the material-liquid ratio is in the range of 1:30-1:50 g/mL. When the material-liquid ratio is 1:30 g/mL, the content of polysaccharide reaches the maximum, which is 66.17%. Therefore, 1:30 g/mL is selected as the optimal material-liquid ratio for the follow-up experiment.

Figure 2:
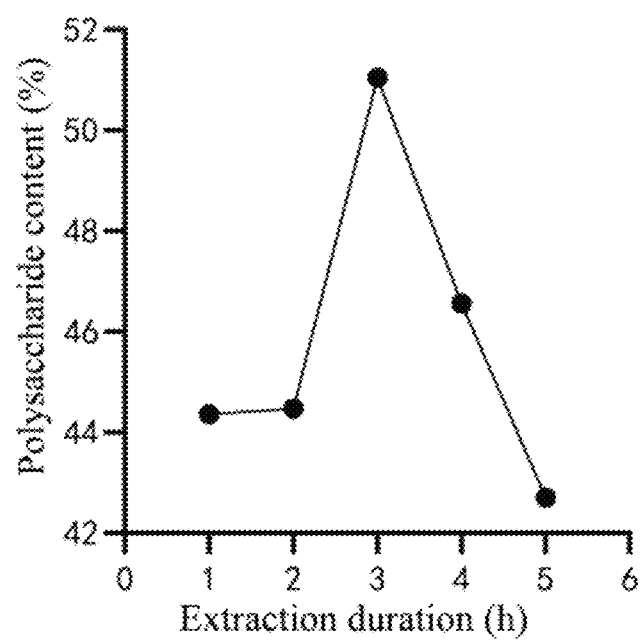
FIG. 2 shows the effect of extraction duration on the extraction rate of polysaccharide.

2.1.1.2 Effect of Extraction Duration of on the Content of *Lyophyllum decastes* Polysaccharide As shown in FIG. 2, the content of *Lyophyllum decastes* polysaccharide increases with the extension of extraction duration when the extraction duration is in the range of 1-3 h, and decreases with the extension of extraction duration when the extraction duration is in the range of 3-5 h. When the extraction duration is 3 h, the content of polysaccharide reaches the highest, which is 51.05%. Therefore, 3 h is selected as the best extraction duration for subsequent experiments.

Figure 3:
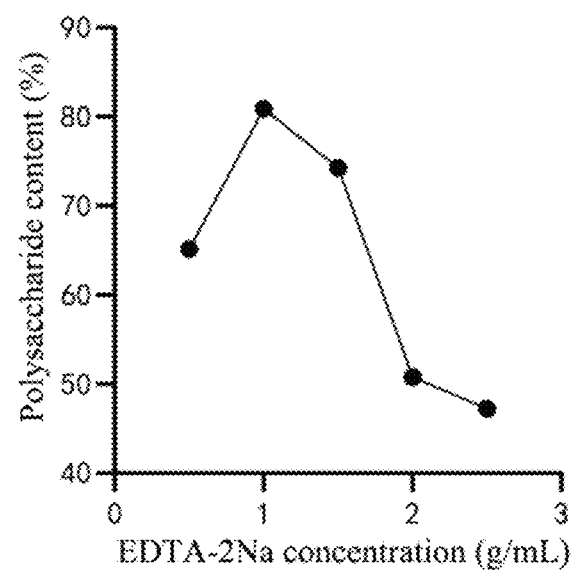
FIG. 3 shows the effect of EDTA-2Na (disodium ethylene diamine tetraacetate) concentration on the extraction rate of polysaccharide.
Figure 4A:
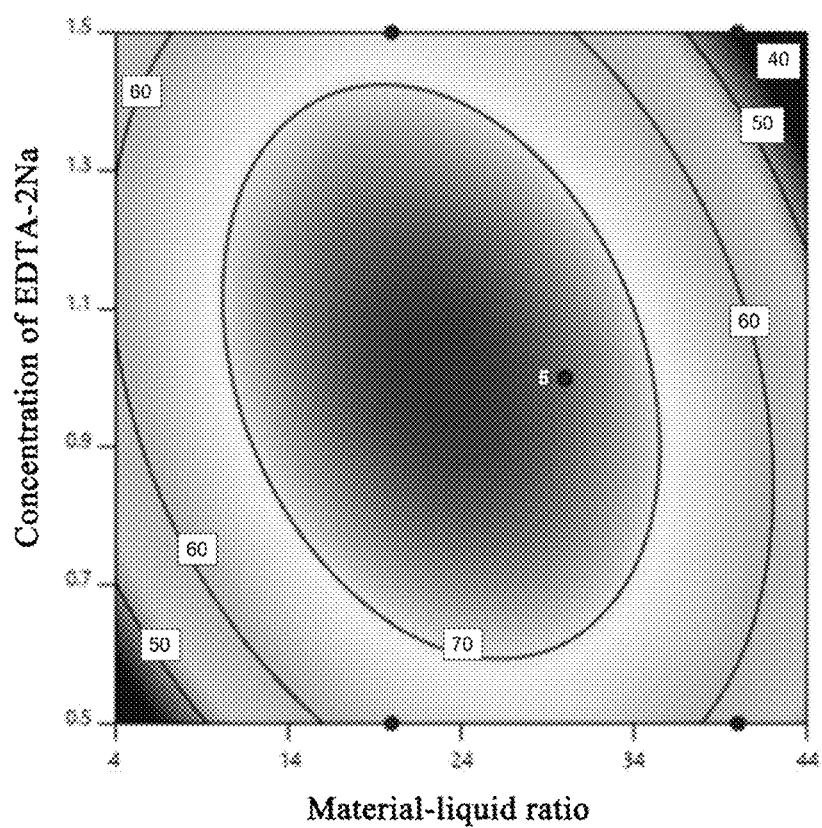
FIG. 4A is a contour map illustrating the effect of interaction between the material-liquid ratio and the concentration of EDTA-2Na on the polysaccharide content.
Figure 4B:
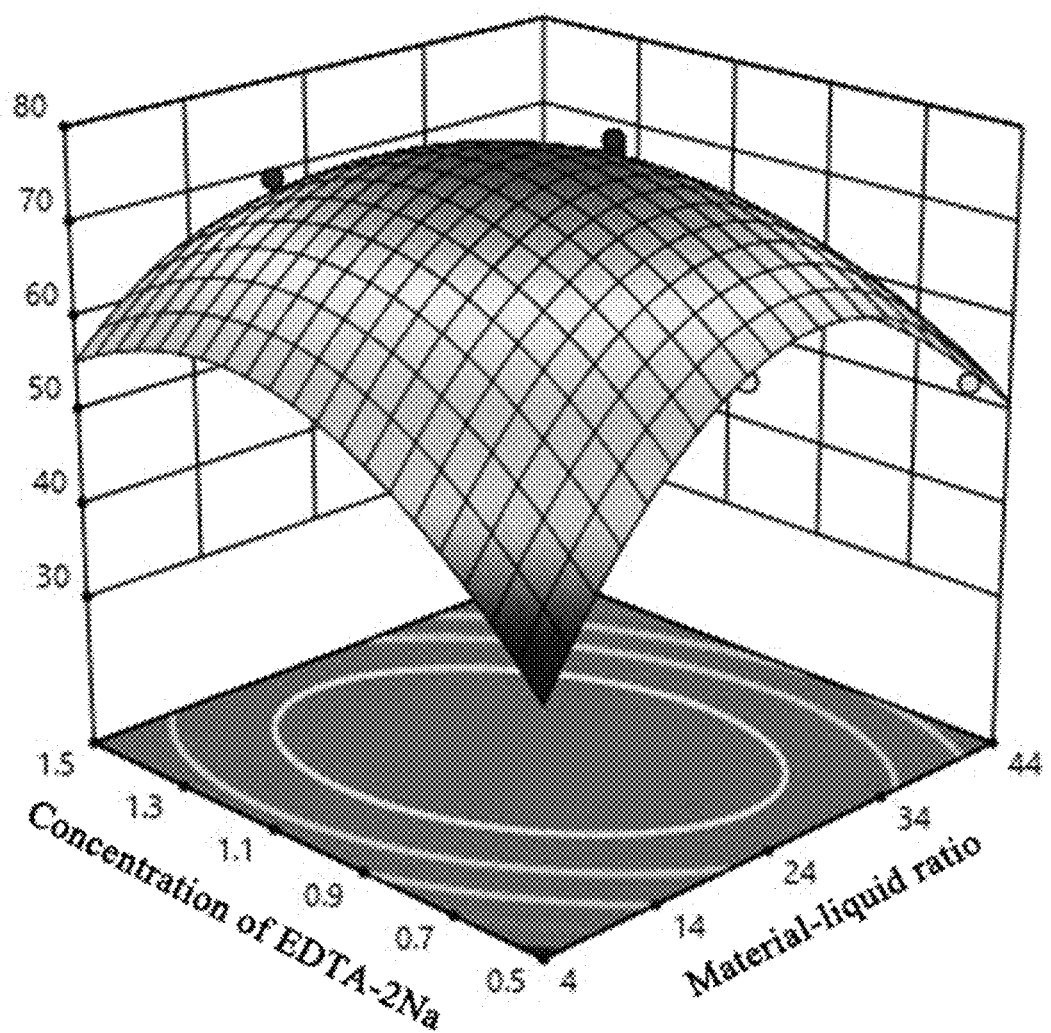
FIG. 4B is a three-dimensional response surface diagram illustrating the effect of interaction between the material-liquid ratio and the concentration of EDTA-2Na on the polysaccharide content.
Figure 5A:
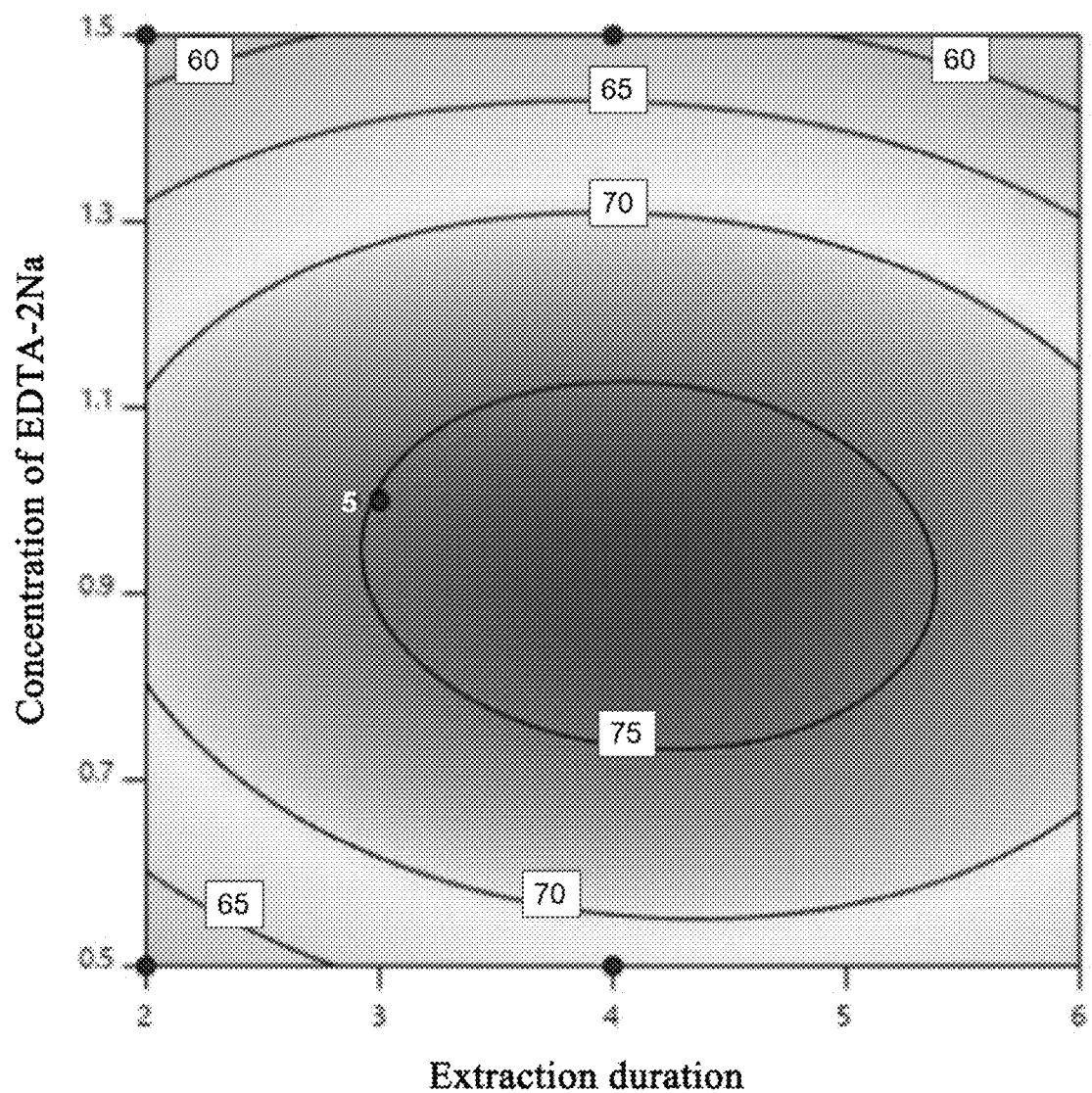
FIG. 5A is a contour map showing the effect of interaction between extraction duration and EDTA-2Na concentration on the polysaccharide content.
Figure 5B:
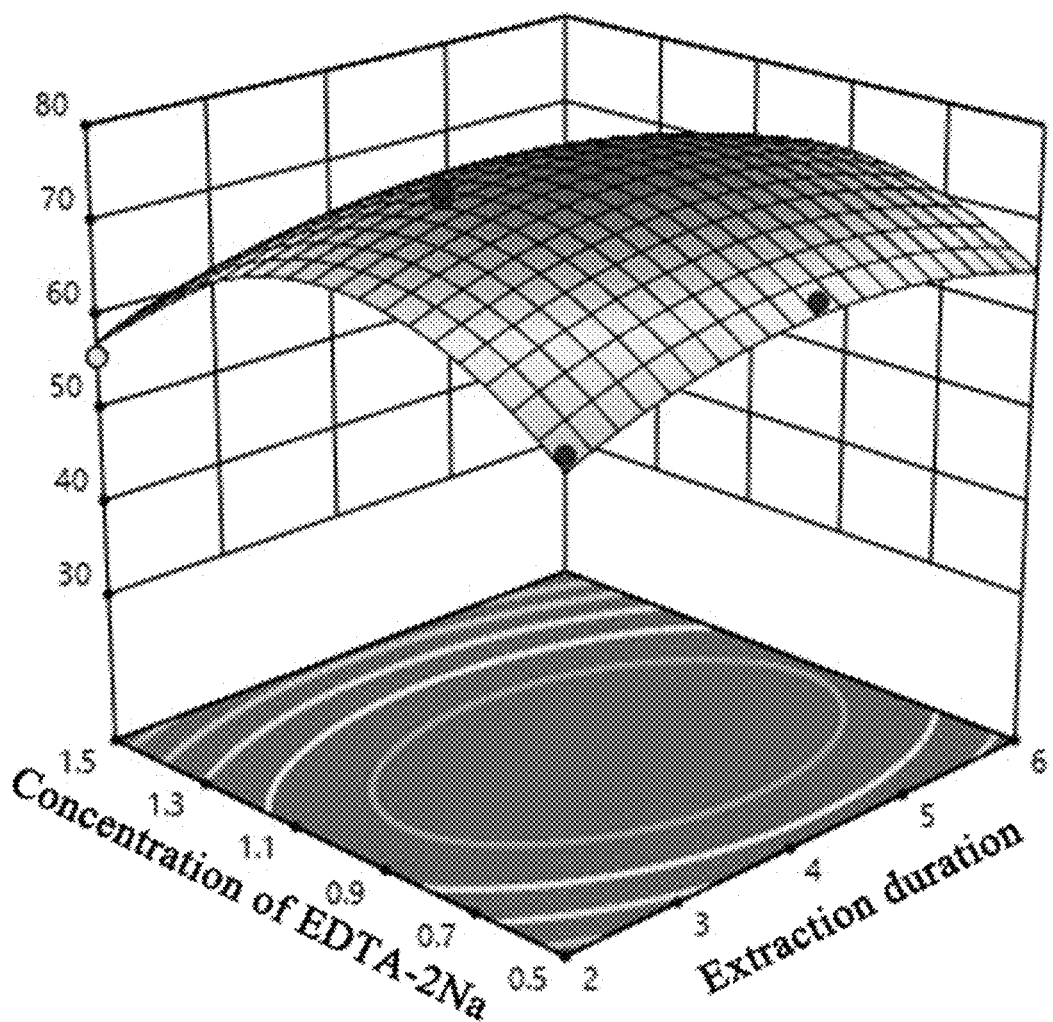
FIG. 5B is a three-dimensional response surface diagram showing the effect of interaction between extraction duration and EDTA-2Na concentration on the polysaccharide content.
Figure 6A:
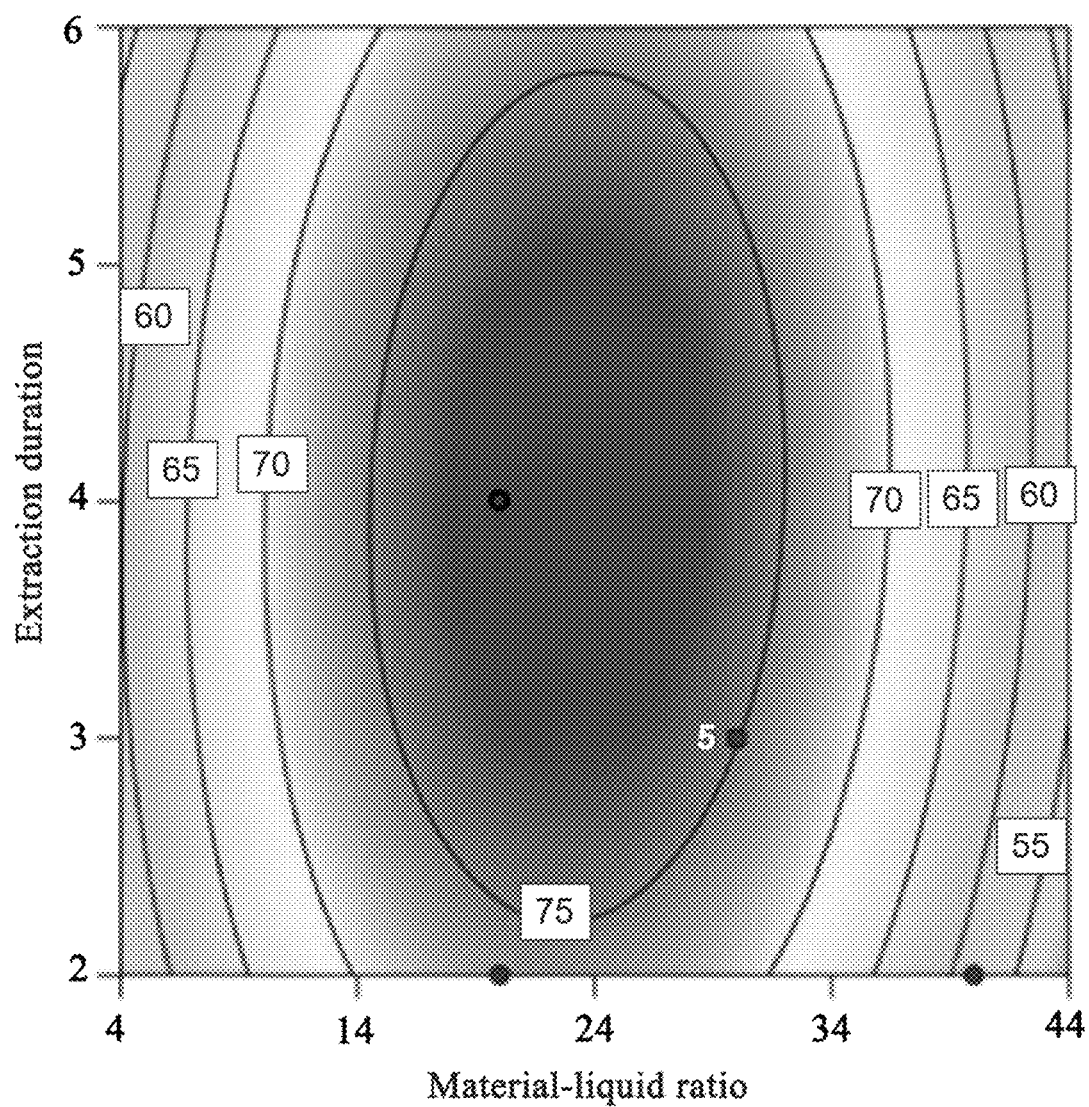
FIG. 6A is a contour map showing the effect of interaction between material-liquid ratio and extraction duration on the polysaccharide content.
Figure 6B:
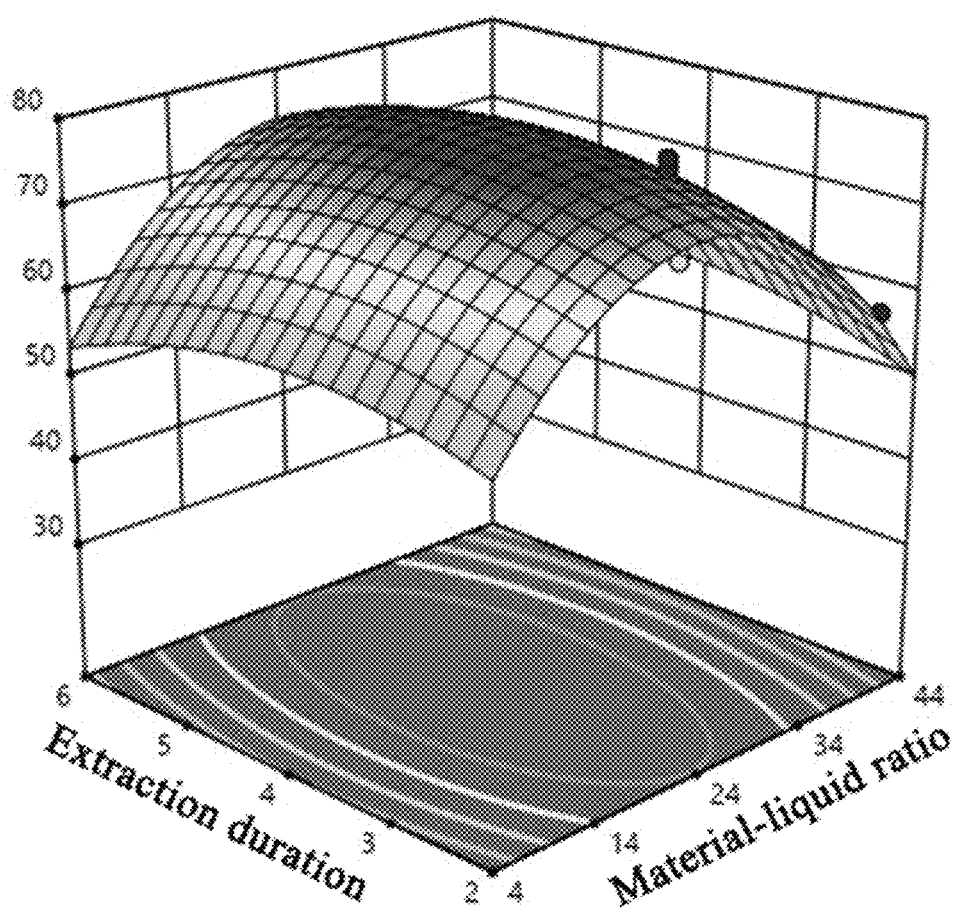
FIG. 6B is a three-dimensional response surface diagram showing the effect of interaction between material-liquid ratio and extraction duration on the polysaccharide content.

2.1.1.3 Effect of EDTA-2Na Concentration in on Content of *Lyophyllum decastes* Polysaccharide As shown in FIG. 3, when the concentration of EDTA-2Na is in the range of 0.5-1 wt %, the content of *Lyophyllum decastes* polysaccharide increases with the increase of EDTA-2Na concentration, and when the concentration of EDTA-2Na increases to 1-2.5%, the content of *Lyophyllum decastes* polysaccharide decreases gradually with the increase of EDTA-2Na concentration. When the concentration of EDTA-2Na is 1 wt %, the content of polysaccharide reaches the highest, which is 80.88%. Therefore, the EDTA-2Na solution with the concentration of 1 wt % is selected for subsequent experiments.

2.1.2 Results of Response Surface Optimization Test

2.1.2.1 Results of Response Surface Test and Analysis of Variance

In this experiment, response surface optimization is carried out on the basis of single factor. According to the design principle of Box-Benhnken experiment, the material-liquid ratio (A), extraction duration (B) and EDTA-2Na concentration (C) are taken as independent variables, and polysaccharide content (Y) is taken as optimization index. The response surface analysis method with three factors and three levels is used to design the extraction experiment, as shown in Table 2. The test data are processed by Design-Expert10.0.

TABLE 2

Design and results of response surface experiment

| Experimental S/N | Material-liquid ratio (g/mL) A | Extraction duration (h) B | EDTA-2Na concentration (g/mL) C | Polysaccharide content (%) |
|---|---|---|---|---|
| 1 | −1 | 1 | 0 | 59.21 |
| 2 | 1 | 1 | 1 | 44.47 |
| 3 | 0 | 0 | 0 | 74.55 |
| 4 | 1 | 0 | 1 | 59.79 |
| 5 | 0 | 0 | 0 | 75.80 |
| 6 | 0 | 0 | 0 | 73.56 |
| 7 | 0 | 0 | 0 | 76.79 |
| 8 | 0 | −1 | 1 | 69.40 |
| 9 | 1 | 1 | 0 | 65.58 |
| 10 | −1 | 0 | −1 | 62.63 |
| 11 | 0 | −1 | −1 | 63.11 |
| 12 | −1 | 0 | 1 | 55.87 |

TABLE 2-continued

Design and results of response surface experiment

| Experimental S/N | Material-liquid ratio (g/mL) A | Extraction duration (h) B | EDTA-2Na concentration (g/mL) C | Polysaccharide content (%) |
|---|---|---|---|---|
| 13 | 0 | 1 | −1 | 54.87 |
| 14 | 1 | 0 | −1 | 69.29 |
| 15 | 1 | −1 | 0 | 77.49 |
| 16 | −1 | −1 | 0 | 72.53 |
| 17 | 0 | 0 | 0 | 74.77 |

The polynomial regression equation between independent variables A, B, C and polysaccharide content Y is:

$$Y = +75.09 - 17.30A + 2.74B - 2.55C + 0.3525AB - 4.17AC - 0.6850BC - 5.16A^2 - 1.23B^2 - 11.97C^2.$$

As shown by the analysis of variance, the P value of this experimental model is less than 0.0001 (P<0.01), which is extremely significant, is statistically significant and good fit and allows for the prediction of polysaccharide content. The P value of the lack of fit in this experiment is 0.06 (P>0.05), which is not significant, indicating that no lack of fit factors exists in the experiment, and the results may therefore be analysed by using this regression equation instead of the true point of the experiment. $R^2 = 0.9769$, indicating that the model explains 97.60% of the variation in response values in the effects of the test factors, and the adjusted coefficient of determination, $R^2\text{Adj} = 0.9472$, is in general consistence with the $R^2$ value. Therefore, the resulting model may thus be used to simulate, analyse and predict the polysaccharide extraction process of Lyophyllum decastes polysaccharide. The P values of A, B, C, AC, $A^2$ and $C^2$ in Table 3 are all less than 0.05, indicating that they have a significant impact on the polysaccharide content, and the P values of A, B, AC and $A^2$ are less than 0.01, indicating that they have a extremely significant impact on the polysaccharide content.

TABLE 3

Analysis of variance of regression model

| Source of variance | Sum of squares | Degree of Freedom | Mean square | F value | P value |
|---|---|---|---|---|---|
| Model | 1375.24 | 9 | 152.80 | 32.88 | <0.0001 |
| A | 426.32 | 1 | 426.32 | 91.73 | <0.0001 |
| B | 60.01 | 1 | 60.01 | 12.91 | 0.0088 |
| C | 51.87 | 1 | 51.87 | 11.16 | 0.0124 |
| AB | 0.4970 | 1 | 0.4970 | 0.1069 | 0.7532 |
| AC | 69.64 | 1 | 69.64 | 14.98 | 0.0061 |
| BC | 1.88 | 1 | 1.88 | 0.4039 | 0.5453 |
| $A^2$ | 112.19 | 1 | 112.19 | 24.14 | 0.0017 |
| $B^2$ | 6.36 | 1 | 6.36 | 1.37 | 0.2802 |
| $C^2$ | 603.24 | 1 | 603.24 | 129.80 | <0.0001 |
| Residual | 32.53 | 7 | 4.65 | | |
| Lack of fit | 26.40 | 3 | 8.80 | 5.74 | 0.0622 |
| Net error | 6.13 | 4 | 1.53 | | |
| Total deviation | 1407.77 | 16 | | | |

Note: P<0.05 indicates significant difference, and P<0.01 indicates extremely significant difference.

2.1.2.2 Response Surface and Contour Analysis

Three-dimensional response surface and contour map fix one of the factors at the same central value, and intuitively reflect the influence of the interaction of the other two factors on polysaccharide content. An elliptical contour and a steep response surface curve indicate that the interaction of the two factors has a greater effect on polysaccharide content. As shown in FIG. 4A, FIG. 4B, FIG. 5A, FIG. 5B, FIG. 6A and FIG. 6B, the contour map of the interaction between the material-liquid ratio and the concentration of EDTA-2Na is elliptical, and the slope is steepest among the response surface curves, indicating that the interaction between the material-liquid ratio and the concentration of EDTA-2Na has a very significant effect on the content of Lyophyllum decastes polysaccharide (P<0.01); the interaction between the extraction duration and the concentration of EDTA-2Na, and the interaction between material-liquid ratio and the extraction duration shows no significant effect on the content of Lyophyllum decastes polysaccharide (P>0.05). The influence of interaction terms on the content of Lyophyllum decastes polysaccharide is material-liquid ratio & concentration of EDTA-2Na>extraction duration & concentration of EDTA-2Na>material-liquid ratio & extraction duration.

The optimal extraction conditions obtained by the software are as follows: the material-liquid ratio is 1:21.99 g/mL, the extraction duration is 2.95 h, and the concentration of EDTA-2Na is 1.04 wt %. Under these conditions, the content of Lyophyllum decastes polysaccharide is predicted to be 77.49%.

2.1.2.3 Optimal Extraction Technology

For the convenience of subsequent experiments, the extraction process is adjusted as follows:
(1) rough extraction: the Lyophyllum decastes is dried and crushed, and passes through a 40-mesh sieve, then the crushed powder of the Lyophyllum decastes is weighed and added with 1 wt % EDTA-2Na aqueous solution according to the liquid-material ratio of 1:22 g/mL, followed by soaking for 2 h at room temperature; then it is put into an ultrasonic instrument for 100 W ultrasonic treatment for 30 min, and extracted for 3 h with extraction temperature set at 98° C.; the extractive solution is centrifugally separated, and the lower residue is again extracted once at 98° C. in a water bath kettle, then the extractive solutions of the two times of extraction are combined and concentrated, followed by adding with 3 times of anhydrous ethanol and staying overnight at 4° C., then centrifuging at 4000 rpm for 10 min, and the precipitate is collected to obtain the crude Lyophyllum decastes polysaccharide; and
(2) refining: the crude Lyophyllum decastes polysaccharide obtained in step (1) is subjected to protein removal and dialyzing, and then freeze-drying to obtain the finished product of Lyophyllum decastes polysaccharide.

2.2 Physical and Chemical Properties of Lyophyllum decastes Polysaccharide 66.79 g of crude polysaccharide is extracted from 1200 g of dry product of Lyophyllum decastes by the optimal extraction process illustrated in 2.1.2.3, and the yield is 5.57%. After the protein is removed by Sevag method, small molecular impurities are removed by dialysis, and the contents of total sugar, reducing sugar, protein and uronic acid are determined. Finally, the LDP with sugar content of 75.47 wt %, protein content of 5.78 wt % and uronic acid content of 8.85 wt % is obtained.

Figure 7:
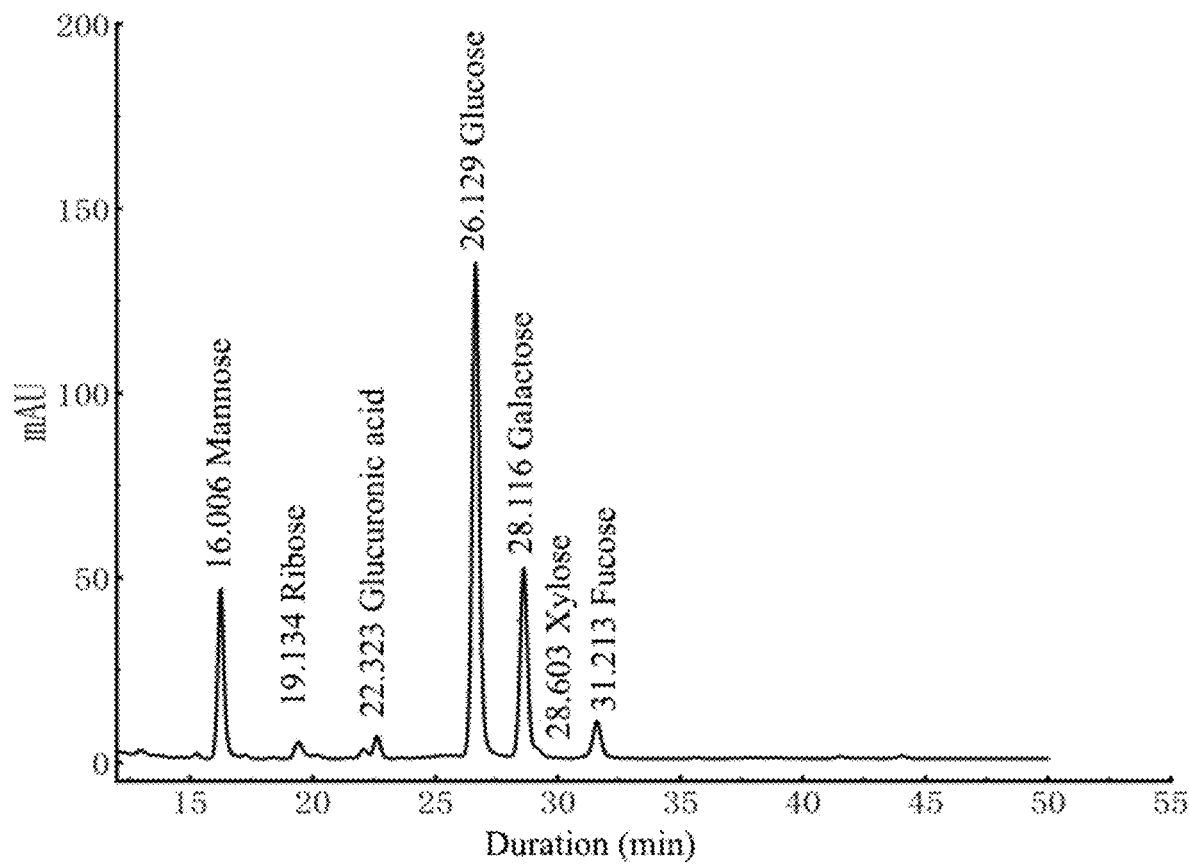
FIG. 7 shows the monosaccharide composition analysis of *Lyophyllum decastes* polysaccharide (LDP).

2.3 Structural Characterization of Lyophyllum decastes Polysaccharide 2.3.1 Monosaccharide Composition The monosaccharide composition of LDP is measured and analyzed in this experiment. The polysaccharide is hydrolyzed into monosaccharide by acid hydrolysis, and monosaccharide derivatives are detected by HPLC after hydrolysis. According to the retention duration of monosaccharide standards, the retention durations of mannose, ribose, glucuronic acid, glucose, galactose, xylose and fucose are 16.006 min, 19.134 min, 22.323 min, 26.129 min, 28.116 min, 28.603 min and 31.213 min, respectively. As comparing to the retention durations of monosaccharide standards, the results show that the LDP is a complex water-soluble polysaccharide mainly composed of glucose and galactose, accompanied by a certain amount of mannose, fucose, glucuronic acid and ribose and a small amount of xylose, and the monosaccharide composition and contents of LDP are shown in Table 4 and FIG. 7.

TABLE 4

Monosaccharide composition and contents of LDP

| Monosaccharide composition | Content (mg/kg) |
|---|---|
| Mannose | 59512.11 |
| Ribose | 11459.15 |
| Glucuronic acid | 15666.48 |
| Glucose | 280495.77 |
| Galactose | 77477.18 |
| Cylose | 3654.08 |
| Fucose | 27337.46 |

2.3.2 Determination of Molecular Weight

Figure 8:
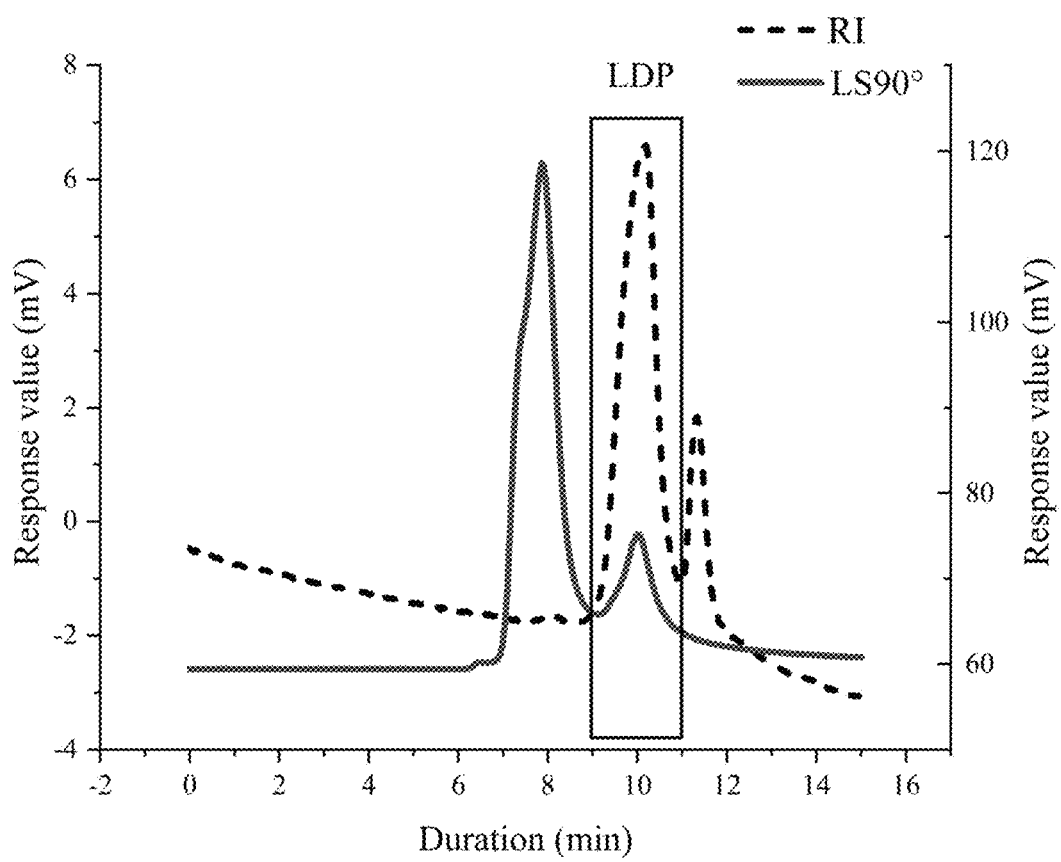
FIG. 8 is a Gel Permeation Chromatograph chart of LDP.

In this experiment, the 1260 Infinity II P multi-detector PGPC/SEC P system is used to measure the molecular weight of LDP. By any combination of differential refraction, light scattering and viscosity measurement, the molecular weights Mp, Mn, Mw, Mz, etc. are obtained by the viscosity and peak time of the sample without relying on the standard and drawing the standard curve, with GPC spectrum as shown in FIG. 8. The purity of the polysaccharide can be obtained on the basis of the relative peak area in the chromatogram, and as shown in Table 5, the retention duration of LDP is 10.117 min, the molecular weight is 51770 g/mol, and the purity reaches 83%.

Table 5 Molecular weight and purity of purified LDP

TABLE 5

Molecular weight and purity of purified LDP

| Sample name | Retention duration (min) | Molecular weight (g/mol) | Purity (%) |
|---|---|---|---|
| LDP | 10.11667 | 51770 | 83% |

2.3.3 Infrared Spectrum Analysis

Figure 9:
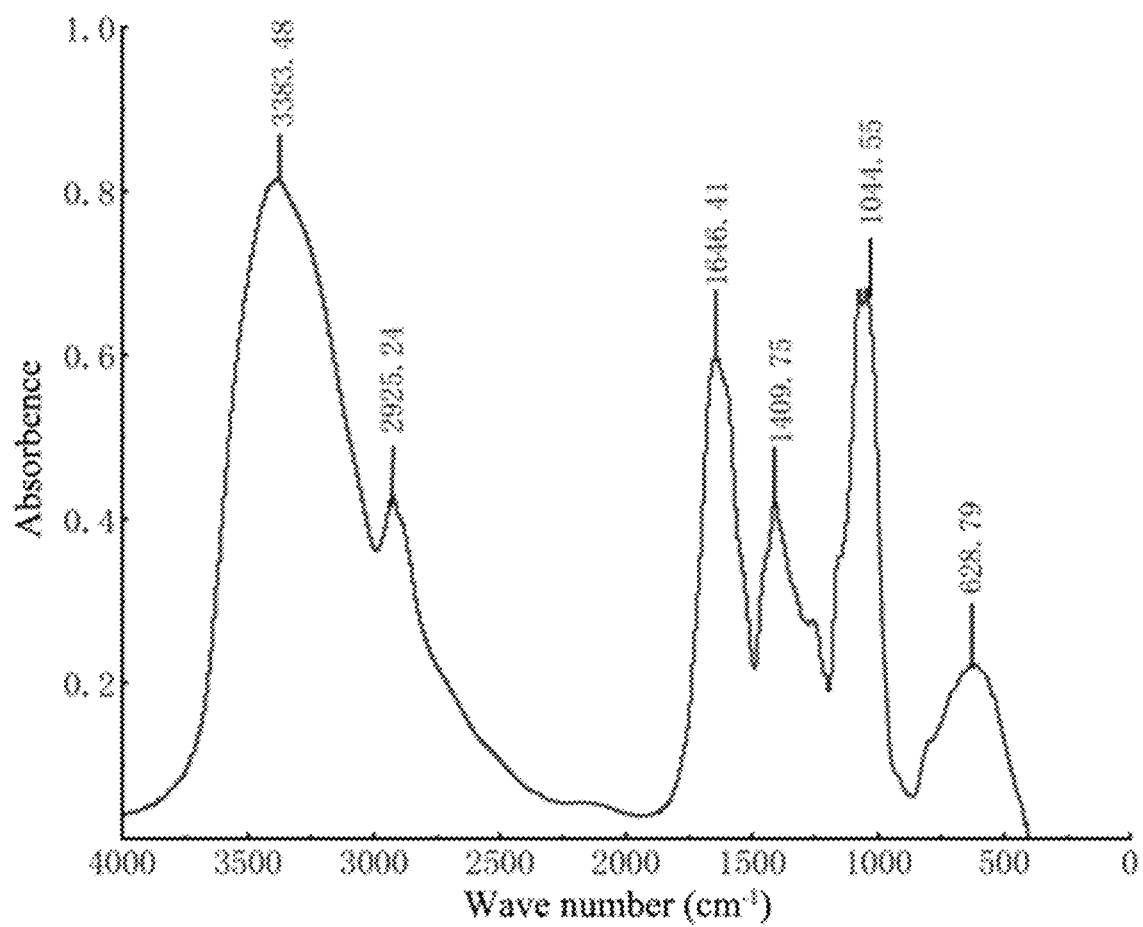
FIG. 9 is an infrared spectrogram of LDP.
Figure 10A:
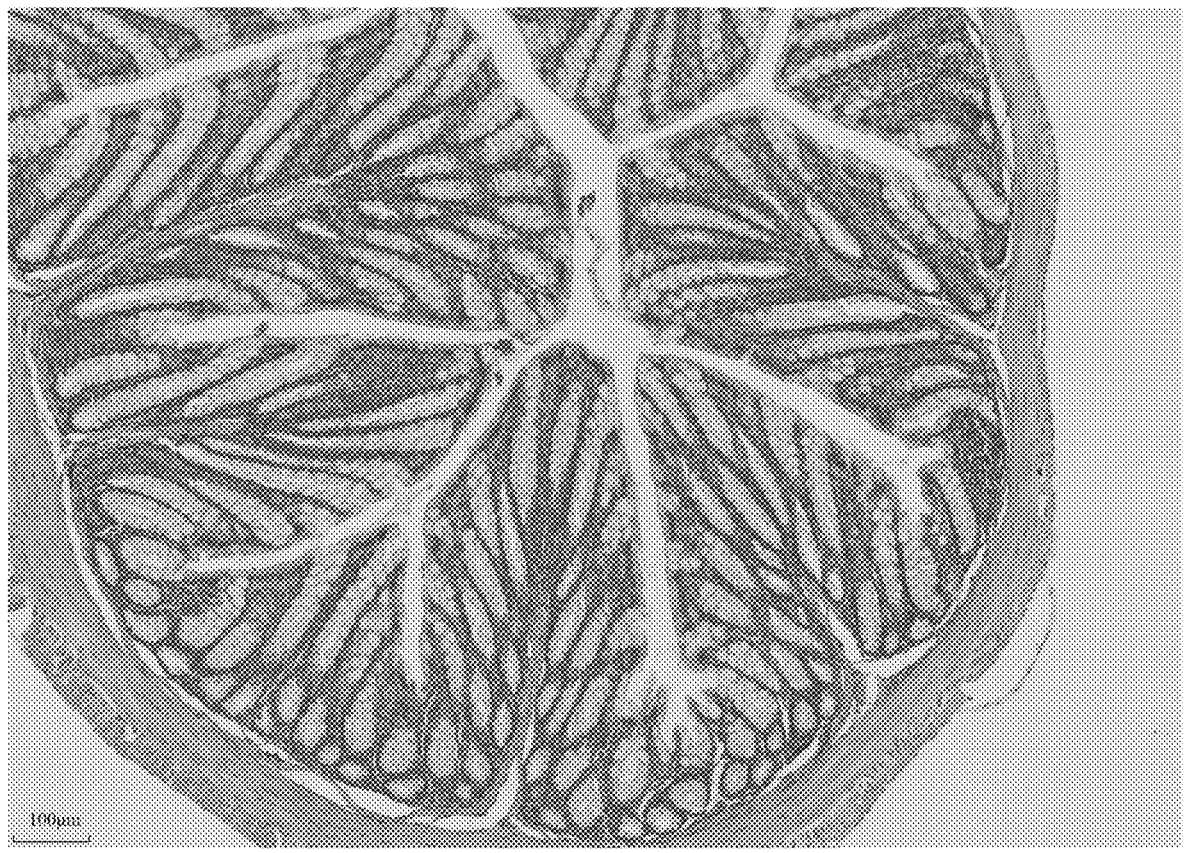
FIG. 10A shows the pathomorphological observation results of mouse colon tissue of CK group.
Figure 10B:
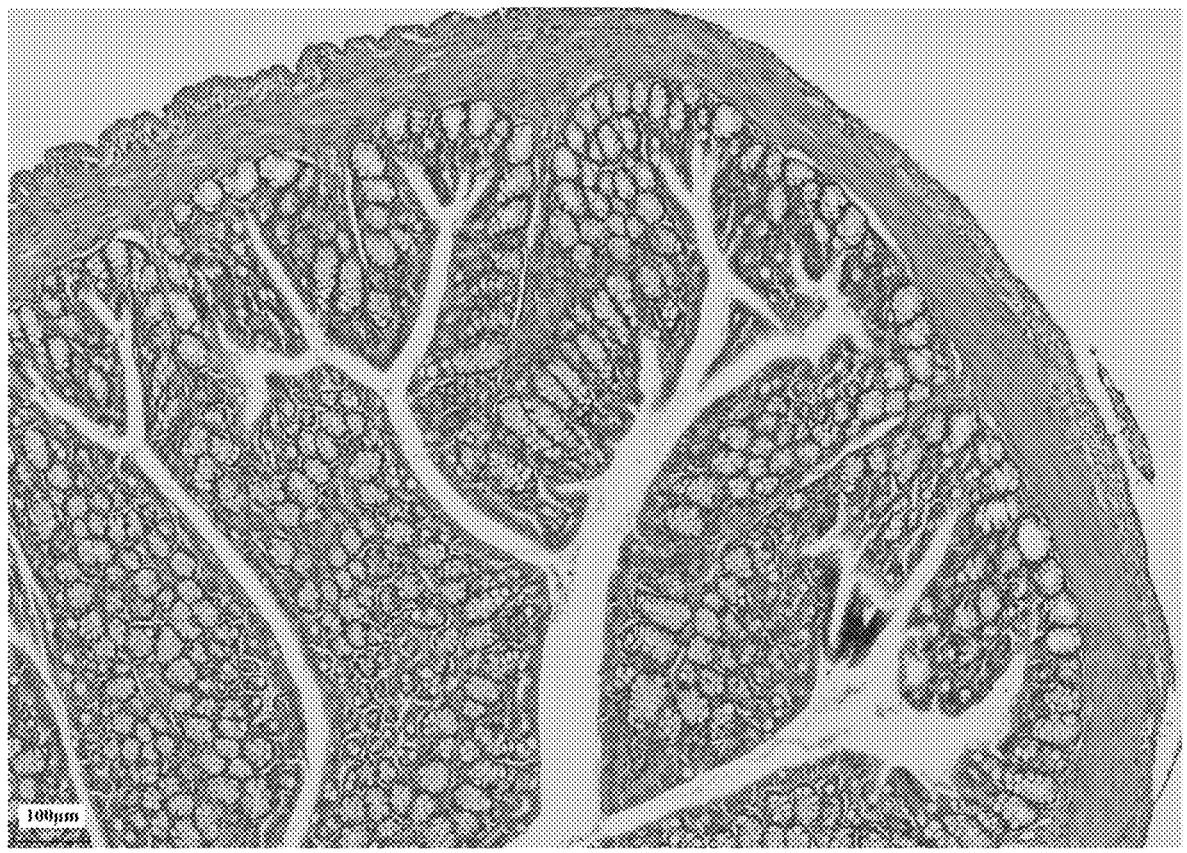
FIG. 10B shows the pathomorphological observation results of mouse colon tissue of Cy group.
Figure 10C:
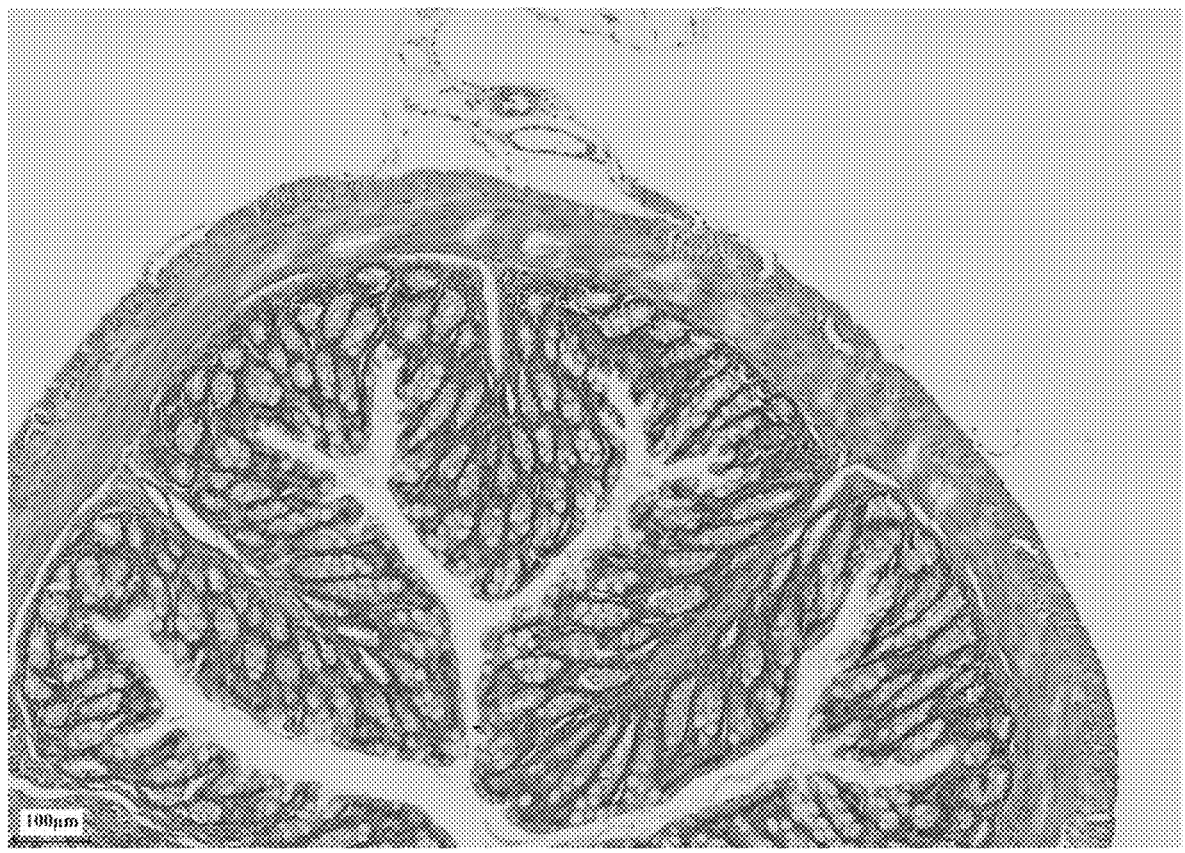
FIG. 10C illustrates the pathomorphological observation results of mouse colon tissue of the group with LDP (100 mg/kg group).
Figure 10D:
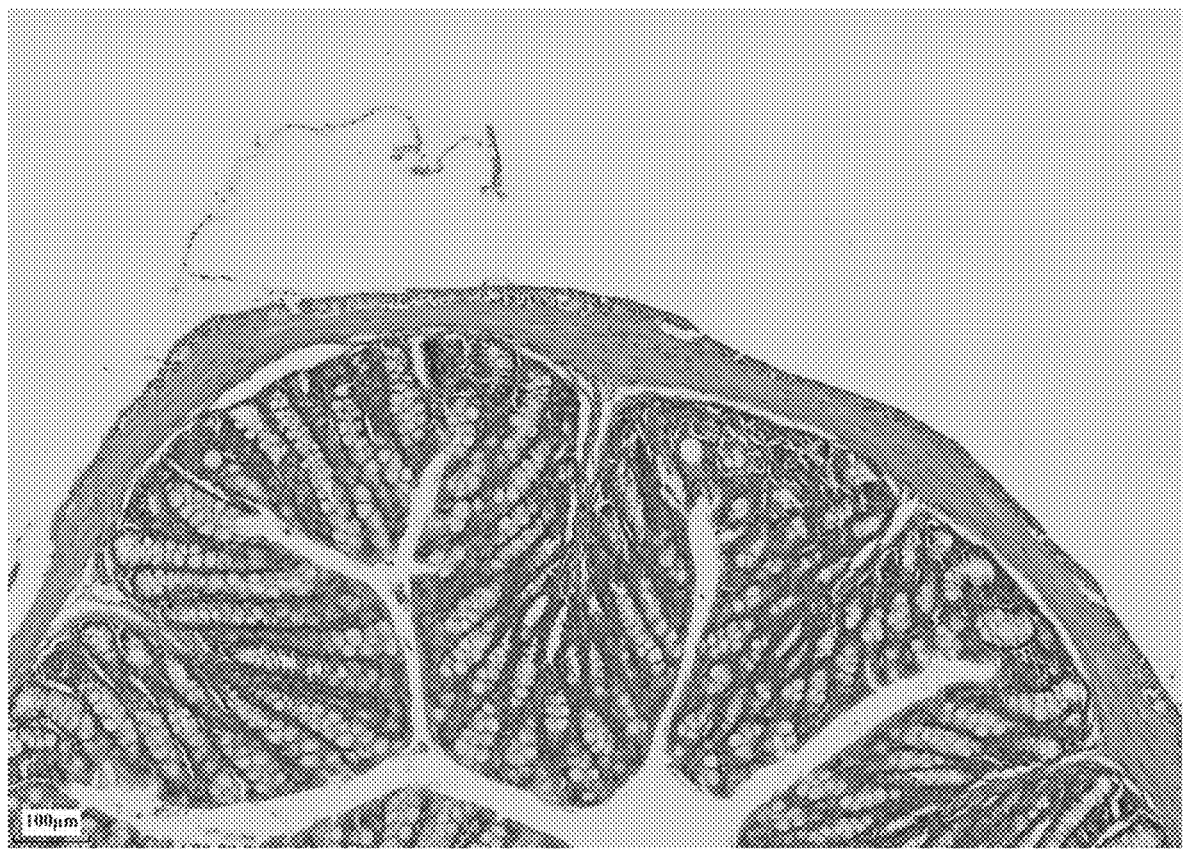
FIG. 10D shows the pathomorphological observation results of mouse colon tissue of the group with LDP (200 mg/kg group).
Figure 10E:
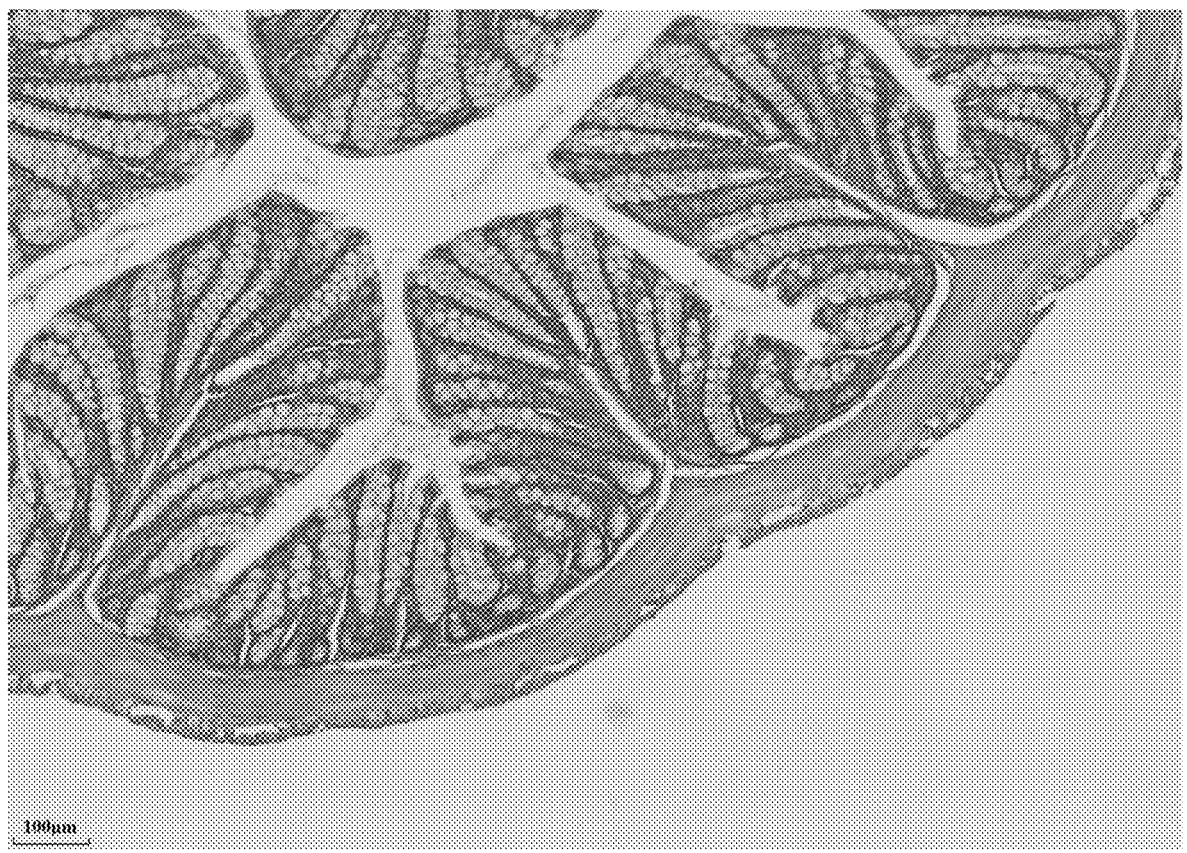
FIG. 10E shows the pathomorphological observation results of mouse colon tissue of the group with LDP (400 mg/kg group).
Figure 10F:
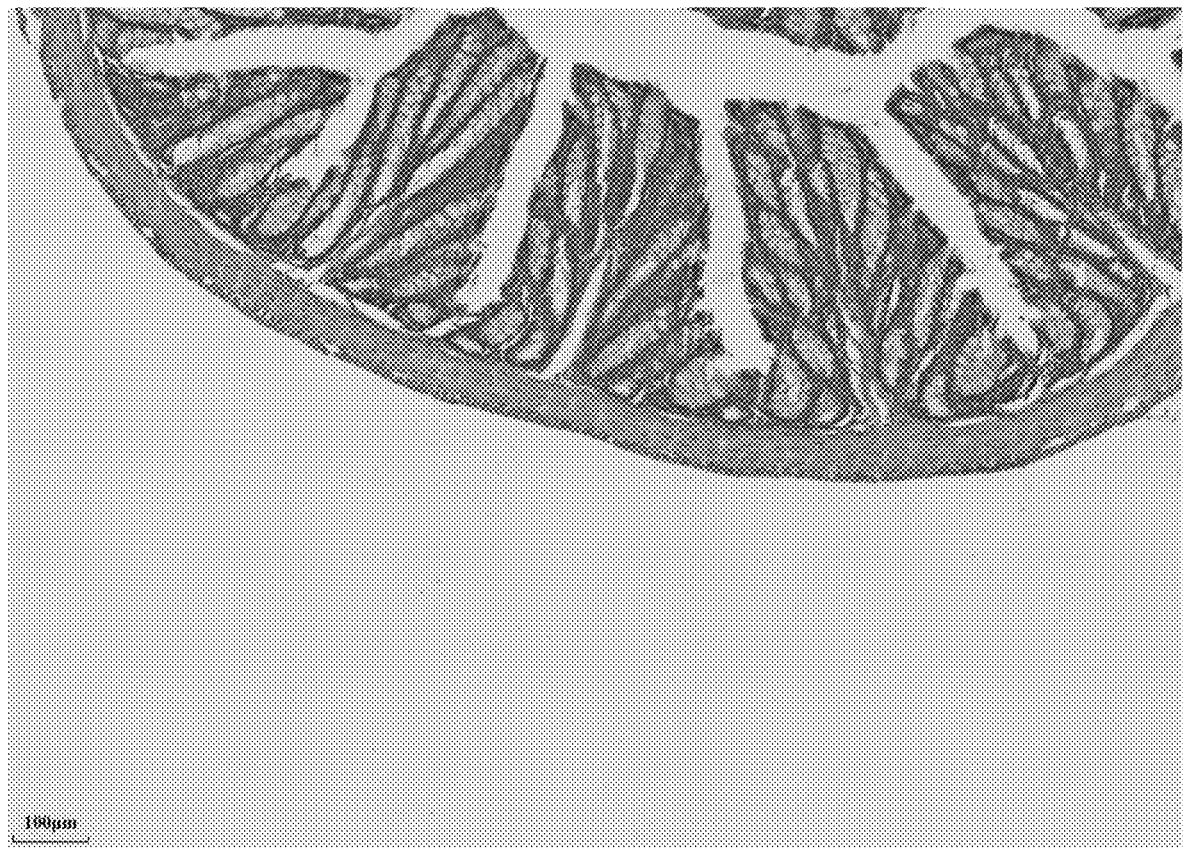
FIG. 10F shows the pathomorphological observation results of mouse colon tissue of the PC group.
Figure 11A:
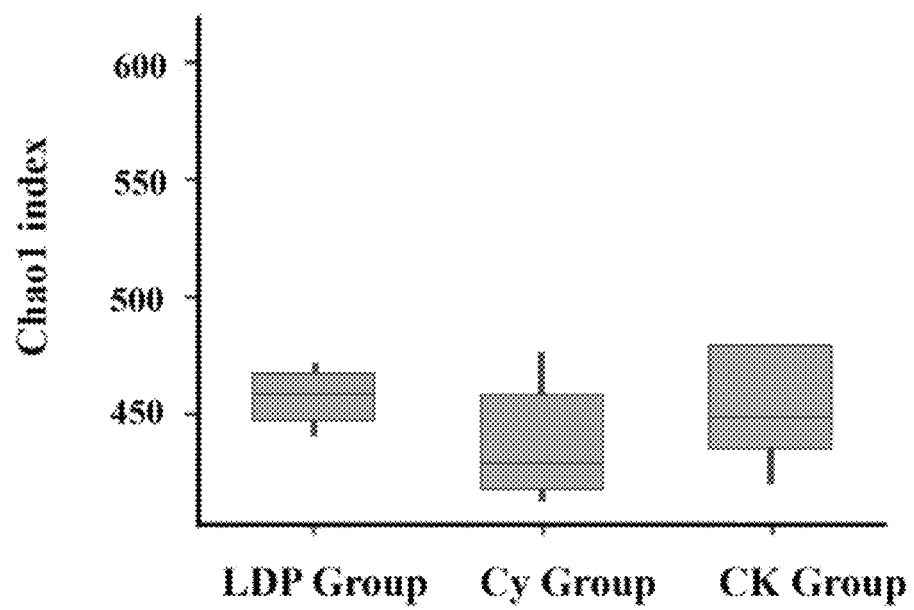
FIG. 11A is a boxplot of Chao 1 index differences among groups at operational taxonomic units (OTU) level.
Figure 11B:
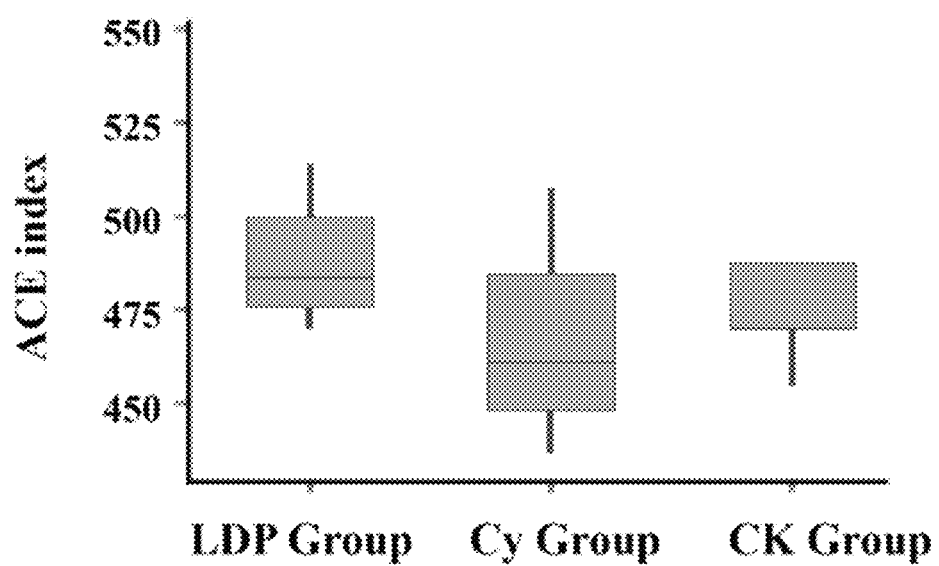
FIG. 11B is a boxplot of ACE index differences among groups at OTU level.
Figure 11C:
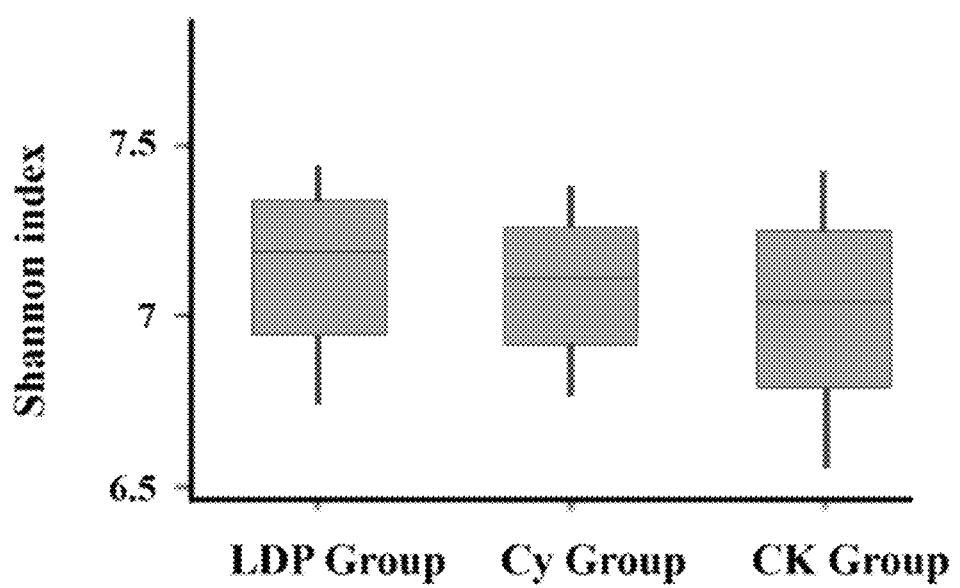
FIG. 11C is a boxplot of Shannon index differences among groups at OTU level.
Figure 11D:
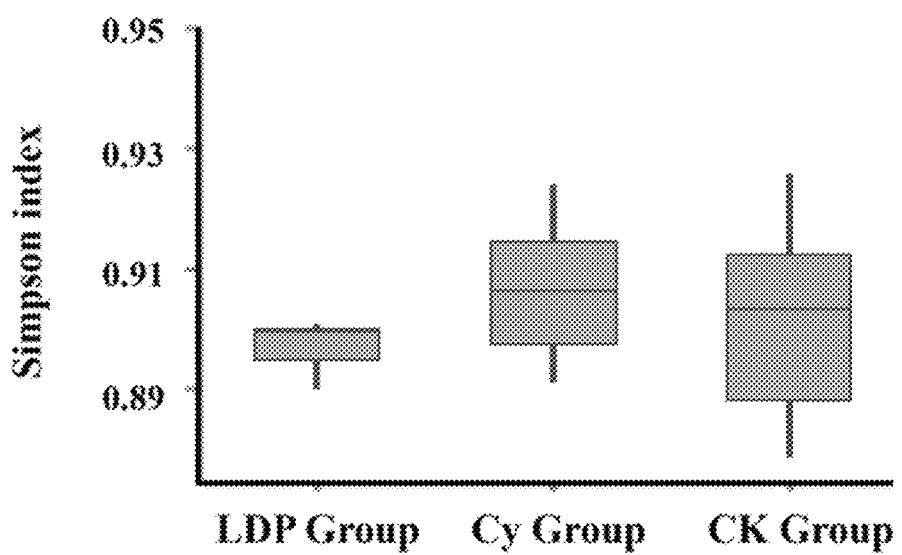
FIG. 11D is a boxplot of Simpson index differences among groups at OTU level.

The structural information of polysaccharides is the theoretical basis for understanding the structure-function relationship of polysaccharides. The study of polysaccharides lags far behind that of nucleic acids and proteins due to the complexity of structures of the polysaccharides, and structural analysis of polysaccharides is therefore an important but challenging task. Infrared spectrum technology is a mature and widely used technology for structural analysis of polysaccharides. There are characteristic absorption peaks of polysaccharides in infrared spectra, and the polysaccharides may be analysed qualitatively and quantitatively according to the positions and shapes of the characteristic peaks, etc., which are mainly used for observing chemical groups and determining glycosidic bonds. As shown in FIG. 9, LDP has strong absorption peaks at 3383.48 $cm^{-1}$ and 2925.24 $cm^{-1}$, which are formed by the stretching vibration of O—H bond and methylene C—H, and are also the characteristic absorption peaks of polysaccharide, indicating that LDP has the characteristics of general polysaccharide. The peaks at 1646.41 $cm^{-1}$ and 1409.75 $cm^{-1}$ may be the results of the stretching vibration of ester carbonyl and carboxyl in polysaccharide. The absorption peak at 1044.55 $cm^{-1}$ indicates the existence of C—O stretching vibration. The absorption peak at 628.79 $cm^{-1}$ indicates the existence of α-glycosidic bonds. Based on the above data, it can be seen that there are several typical characteristic absorption peaks of polysaccharides in LDP.

Embodiment 2

1. Methods 1.1 Animal Experiment Design and Treatment 1.1.1 Animal Grouping

Eighty 6-week-old KM male mice are taken and feed adaptively for 7 days, then 10 mice are randomly selected and labelled as blank control group (CK), 15 mice are randomly taken and labelled as the model group (Cy), and 45 mice are randomly taken and labelled as the administered group (LDP), which are equally divided into three groups, namely, the low-dose group (100 mg/kg), the medium-dose group (200 mg/kg), and the high-dose group (400 mg/kg), and the remaining 10 mice are labelled as the positive control group (PC).

1.1.2 Establishment of Immunocompromised Mouse Model and Drug Intervention

The CK group is given 80 mg/kg normal saline every day. Cy group, PC group and LDP group are intraperitoneally injected with cyclophosphamide (80 mg/kg) for 7 consecutive days, and then given saline 80 mg/kg, levamisole hydrochloride 40 mg/kg and different doses of solution of *Lyophyllum decastes* polysaccharide, namely, 100 mg/kg for low-dose group, 200 mg/kg for medium-dose group and 400 mg/kg for high-dose group respectively. During the experiment, the drug is given once a day for 28 days, and the weight changes of each group of mice are measured and recorded daily.

1.1.3 Animal Treatment and Sample Collection 24 hours after the final administration, mice in each group are weighed, recorded, and executed by cervical dislocation. After execution, blood is immediately taken from the eye socket and the mice are dissected, the collected whole blood is centrifuged twice (3500 rpm) at 4° C. for 10 min each time, and the supernatant is taken. The serum is stored in the ultra-low temperature refrigerator at −80° C. The isolated thymus, spleen, small intestine, cecum, and cecum contents are weighed and recorded and stored in an ultra-low temperature refrigerator at −80° C. The colon is fixed using paraformaldehyde.

1.2 Immune Organ Index

The thymus and spleen indexes of mice are expressed by the ratio of the weight of thymus or spleen (mg) to the weight of mice (g).

1.3 Observation of Colon Histomorphology

The colon tissue fixed with paraformaldehyde is dehydrated in ethanol solution according to the gradient of low concentration to high concentration, that is, 70% (2 h), 80% (overnight), 90% (2 h), 100% I (1 h) and 100% II (1 h), and then it is subjected to transparent treatment with pure xylene. The tissue block after transparent treatment is placed into the mixed solution of paraffin and xylene with the same volume for 15 min, then placed into pure paraffin for 30 min for embedding. The embedded tissue wax blocks are cut into thin slices of the desired section thickness, pasted onto slides and dried in a thermostat. The slices are dewaxed twice by xylene, followed by placed in gradient ethanol (95%, 85%, 75%) of high concentration to low concentration for 5 min, placed in distilled water for 3 min, dyed with hematoxylin dye solution and eosin dye solution, placed in 95% ethanol for washing off excess red and placed in anhydrous ethanol for 5 min. The slices are put into the mixed solution of ethanol and xylene with the same volume for 5 min, and then put into pure xylene for transparency twice. Finally, the slices are sealed with neutral gum, and placed in an upright microscope camera system to take pictures. The target area of tissue is selected for for imaging at 100 times and 400 times respectively, and the imaging is done in such a way that the tissue fills the entire field of view as much as possible, ensuring that the background light is consistent in each photograph.

1.4 Detection of Antioxidant Capacity

Small intestine tissue of mice is cut into pieces, added with 9 times of normal saline, crushed on ice and centrifuged to make 10 wt % tissue homogenate. The serum is diluted with normal saline to a suitable concentration, and the levels of serum and tissue homogenate are determined according to the instructions of SOD, MDA, CAT and GSH-Px detection kits.

1.5 Detection of Serum Indicators

The contents of interleukin (IL-1B), tumor necrosis factor (TNF-α) and immunoglobulin A (sIgA) in serum samples of mice are determined by double antibody sandwich method with Jingmei kit.

1.6 Microbial Diversity Analysis 16S rRNA sequencing technology is used to study the effect of *Lyophyllum decastes* polysaccharide on intestinal flora of cyclophosphamide-treated mice, and the sequencing data are analyzed by online platform BMKCloud (https://www.biocloud.net). The species diversity in a single sample is studied by Alpha diversity analysis, and the Ace, Chao 1, Shannon and Simpson indexes of each sample are counted, and the sample dilution curve and grade abundance curve are plotted. Beta diversity analysis is used to compare the differences in species diversity (community composition and structure) of different samples. Through the significant analysis of the differences between groups, the differences of species abundance composition between different sample groups are further measured.

2. Results

2.1 Changes of Body Weight and Immune Organ Index in Mice

Changes in body weights of mice in LDP administrated group of different dosage, CK group and PC group are illustrated in Table 6. Compared with the model group, changes in body weights of mice in *Lyophyllum decastes* administrated groups of different dosage and blank control group are not significant, although there is an increasing tendency.

TABLE 6

Effect of LDP on the weight change of mice (X ± s, n = 10)

| Groups | Initial weight | After modeling | 14 days | 21 days | 28 days |
| --- | --- | --- | --- | --- | --- |
| CK | 36.59 ± 0.96 | 38.25 ± 0.91 | 39.91 ± 1.12 | 41.88 ± 1.09 | 42.14 ± 0.89 |
| Cy | 38.60 ± 0.44 | 37.33 ± 0.54 | 38.92 ± 0.74 | 39.46 ± 0.69 | 41.23 ± 0.59 |
| LDP (100 mg/kg) | 37.83 ± 0.81 | 36.23 ± 0.65 | 37.44 ± 0.58 | 39.06 ± 0.67 | 41.89 ± 0.73 |
| LDP (200 mg/kg) | 37.49 ± 0.73 | 36.71 ± 0.59 | 37.58 ± 0.65 | 39.76 ± 0.68 | 42.16 ± 0.67 |
| LDP (400 mg/kg) | 38.09 ± 0.62 | 37.14 ± 0.66 | 38.29 ± 0.70 | 40.15 ± 0.77 | 43.01 ± 0.86 |
| PC | 37.84 ± 0.67 | 36.27 ± 1.04 | 37.97 ± 0.82 | 39.70 ± 0.77 | 41.45 ± 0.69 |

Note: compared with the normal control group, * means significant difference (P<0.05) and ** means extremely significant difference (P<0.01); compared with the model control group, #means significant difference (P<0.05) and ##means extremely significant difference (P<0.01). CK: blank control group; Cy: model group.

2.2 Effect of LDP on Immune Organ Index of Mice

The effect of LDP on immune organ index of mice is shown in Table 7. Compared with CK group, the indexes of thymus and spleen in Cy group is decreased significantly (P<0.01), which indicates that immune organ atrophy in healthy mice is successfully induced in Cy group, thus proving that the model of hypoimmunity is successful. Compared with Cy group, the indexes of thymus and spleen of mice in each administrated group are increased, which is positively correlated with the dosage, but the growth index is not significant (P>0.05). From the comparison of the data of each group, it is found that the effect of LDP on spleen is higher than that on thymus. Collectively, all the above data demonstrate that LDP intervention is effective in increasing the immune organ index of immunocompromised mice, reversing induced thymic and splenic atrophy in Cy group, and thus enhancing the organismal immunity of mice.

TABLE 7

Effect of LDP on immune organ index of mice (X ± s, n = 10)

| Groups | thymus index (mg/kg) | spleen index (mg/kg) |
|---|---|---|
| CK | 1.85 ± 0.36 | 2.28 ± 0.51 |
| Cy | 0.88 ± 0.28** | 1.04 ± 0.13** |
| LDP (100 mg/kg) | 0.91 ± 0.34 | 1.06 ± 0.18 |
| LDP (200 mg/kg) | 1.04 ± 0.23 | 1.11 ± 0.07 |
| LDP (400 mg/kg) | 1.10 ± 0.34 | 1.12 ± 0.11 |
| PC | 1.04 ± 0.29 | 1.24 ± 0.17## |

Note: compared with the normal control group, * means significant difference (P<0.05) and ** means extremely significant difference (P<0.01); compared with the model control group, #means significant difference (P<0.05) and ##means extremely significant difference (P<0.01). CK: blank control group; Cy: model group.

2.3 Observation of Colon Histomorphology

See FIGS. 10A-FIG. 10F for the histopathological observation results of colon tissue of mice in LDP administrated groups of different dosage, CK groups and PC groups. In CK group, the structure of each layer of colon tissue is clear, and the epithelial cells of mucosa are arranged tightly and regularly, with no cell shedding observed; there are abundant goblet cells and glands, a small amount of blood vessels can be observed in lamina propria, muscle cells are arranged neatly, and no thickness change is found. In Cy group, the morphology of intestinal tissue is relatively intact, the surface of mucosal layer is slightly uneven, and the arrangement of columnar cells is slightly disordered, the number of goblet cells and glands is abundant, and the length of glands is slightly shorter; compared with the normal group, the cells are irregularly arranged with changed morphology. The colon tissue of mice in administrated groups with different dosage has clear structure, especially in the high-dose group (LDP) (400 mg/kg), the surface of mucosa is smooth and slightly damaged, columnar cells are arranged regularly, goblet cells are abundant, and intestinal glands are numerous and long; no obvious pathological changes are found in the muscular layer, and the overall pathological changes are not significant. Compared with CK group, the intestinal tissue structure of PC group is clearer, the surface of mucosa layer is not smooth, the damage is relatively obvious, the epithelial columnar cells are relatively dense, a large number of goblet cells and intestinal glands can be seen, and the intestinal glands are shorter than the blank control group, some intestinal gland cells are broken, and the number of cells in lamina propria is slightly increased, and the pathological changes of muscular layer are not significant. All the above experimental data prove that LDP is effective in repairing the colon tissue damage of immunocompromised mice induced in Cy group and improving the immune ability of the body.

2.4 Antioxidant Capacity

The activities of SOD, CAT, GSH-Px and MDA in serum and small intestine of Cy-induced immunocompromised mice are shown in Table 8 and Table 9 respectively. The results show that the *Lyophyllum decastes* polysaccharide can effectively increase the levels of SOD, CAT and GSH-Px in serum and small intestine of immunocompromised mice, and effectively decrease the content of MDA, thus enhancing the antioxidant effect of immune organs in immunocompromised mice.

TABLE 8

Effect of LDP on serum antioxidant capacity in immunocompromised mice

| Groups | MDA (nmol/mL) | SOD (U/mL) | CAT (U/mL) | GSH-Px (U/mg) |
|---|---|---|---|---|
| CK | 0.33 ± 0.16 | 36.85 ± 2.81 | 7.63 ± 1.54 | 311.53 ± 23.87 |
| Cy | 1.79 ± 0.31** | 30.00 ± 2.69** | 4.32 ± 0.72** | 115.93 ± 11.79** |
| LDP (100 mg/kg) | 1.32 ± 0.38## | 34.93 ± 1.25## | 13.44 ± 1.72## | 304.41 ± 17.24## |
| LDP (200 mg/kg) | 1.27 ± 0.29# | 35.06 ± 1.76## | 14.47 ± 0.58## | 308.14 ± 7.80## |
| LDP (400 mg/kg) | 0.34 ± 0.09## | 40.09 ± 0.27## | 16.43 ± 2.54## | 346.78 ± 8.89## |
| PC | 0.59 ± 0.22## | 36.52 ± 1.49## | 9.30 ± 1.09## | 336.95 ± 15.79## |

Note: compared with the normal control group, * means significant difference (P<0.05) and ** means extremely significant difference (P<0.01); compared with the model control group, #means significant difference (P<0.05) and ##means extremely significant difference (P<0.01). CK: blank control group; Cy: model group.

TABLE 9

Effect of LDP on antioxidant capacity of small intestine in immunocompromised mice

| Groups | MDA (nmol/mg prot) | SOD (U/mg prot) | CAT (U/mg prot) | GSH-Px (U/mg prot) |
|---|---|---|---|---|
| CK | 2.91 ± 0.30 | 87.36 ± 7.58 | 38.08 ± 3.39 | 3697.27 ± 610.95 |
| Cy | 6.43 ± 0.53** | 53.14 ± 3.25** | 31.68 ± 5.11* | 2361.96 ± 485.25** |
| LDP (100 mg/kg) | 5.64 ± 0.47# | 73.32 ± 5.35## | 45.42 ± 5.29## | 3534.84 ± 725.40## |
| LDP (200 mg/kg) | 4.71 ± 049## | 88.55 ± 5.96## | 47.34 ± 6.47## | 3572.36 ± 334.66## |
| LDP (400 mg/kg) | 4.17 ± 0.47## | 103.99 ± 4.79## | 62.02 ± 9.15## | 4081.42 ± 784.50## |
| PC | 3.56 ± 0.68## | 93.20 ± 4.48## | 48.29 ± 5.21## | 3653.90 ± 633.73## |

Note: compared with the normal control group, * means significant difference (P<0.05) and ** means extremely significant difference (P<0.01); compared with the model control group, #means significant difference (P<0.05) and ##means extremely significant difference (P<0.01). CK: blank control group; Cy: model group.

2.5 Inflammatory Factors

The detection results of cytokines in serum and small intestine of immunocompromised mice are illustrated in Table 10 and Table 11 respectively. The results show that the contents of inflammatory factors IL-1B and TNF-α in serum and small intestine of Cy group mice are increased significantly, and the levels of IL-1B and TNF-α are decreased by the *Lyophyllum decastes* polysaccharide, which improves the inflammation of immunocompromised mice.

TABLE 10

Effect of LDP on serum cytokines in immunocompromised mice

| Groups | IL-1β | TNF-α |
|---|---|---|
| CK | 19.59 ± 1.59 | 102.16 ± 8.64 |
| Cy | 12.09 ± 2.83** | 73.04 ± 12.08** |
| LDP (100 mg/kg) | 12.76 ± 2.30## | 78.71 ± 14.14 |
| LDP (200 mg/kg) | 16.73 ± 0.79## | 89.11 ± 6.66# |
| LDP (400 mg/kg) | 19.27 ± 1.63## | 95.32 ± 12.62## |
| PC | 17.00 ± 1.96## | 83.60 ± 12.15 |

Note: compared with the normal control group, * means significant difference (P<0.05) and ** means extremely significant difference (P<0.01); compared with the model control group, #means significant difference (P<0.05) and ##means extremely significant difference (P<0.01). CK: blank control group; Cy: model group.

TABLE 11

Effect of LDP on the level of small intestinal cytokines in immunocompromised mice

| Groups | IL-1β | TNF-α |
|---|---|---|
| CK | 22.69 ± 1.48 | 122.04 ± 6.82 |
| Cy | 13.72 ± 2.79 | 74.77 ± 12.57 ** |
| LDP (100 mg/kg) | 15.04 ± 1.60 ## | 91.64 ± 4.19 ## |
| LDP (200 mg/kg) | 15.24 ± 1.03 ## | 93.16 ± 10.36 # |
| LDP (400 mg/kg) | 19.50 ± 1.69 ## | 94.27 ± 11.33 # |
| PC | 17.45 ± 1.69 ## | 82.55 ± 11.39 |

Note: compared with the normal control group, * means significant difference (P<0.05) and ** means extremely significant difference (P<0.01); compared with the model control group, #means significant difference (P<0.05) and ##means extremely significant difference (P<0.01). CK: blank control group; Cy: model group.

2.6 Immunoglobulin (sIgA

The detection results of sIgA in serum and small intestine of immunocompromised mice are shown in Table 12. The results show that the secretion level of sIgA in serum and small intestine of Cy group mice is significantly reduced, while the *Lyophyllum decastes* polysaccharide can effectively promote the secretion of sIgA in serum of immunocompromised mice.

TABLE 12

Effect of LDP on sIgA in serum and small intestine of immunocompromised mice

| Groups | Serun (μg/mL) | Small intestine (μg/mL) |
|---|---|---|
| CK | 3.90 ± 0.52 | 4.02 ± 0.62 |
| Cy | 1.37 ± 0.21** | 1.93 ± 0.38** |
| LDP (100 mg/kg) | 1.47 ± 0.17 | 2.14 ± 0.50 |
| LDP (200 mg/kg) | 2.09 ± 0.14## | 2.94 ± 0.52## |
| LDP (400 mg/kg) | 2.54 ± 0.60## | 3.10 ± 0.15## |
| PC | 2.90 ± 0.40## | 3.12 ± 0.24## |

Note: compared with the normal control group, * means significant difference (P<0.05) and ** means extremely significant difference (P<0.01); compared with the model control group, #means significant difference (P<0.05) and ##means extremely significant difference (P<0.01). CK: blank control group; Cy: model group.

Figure 12:
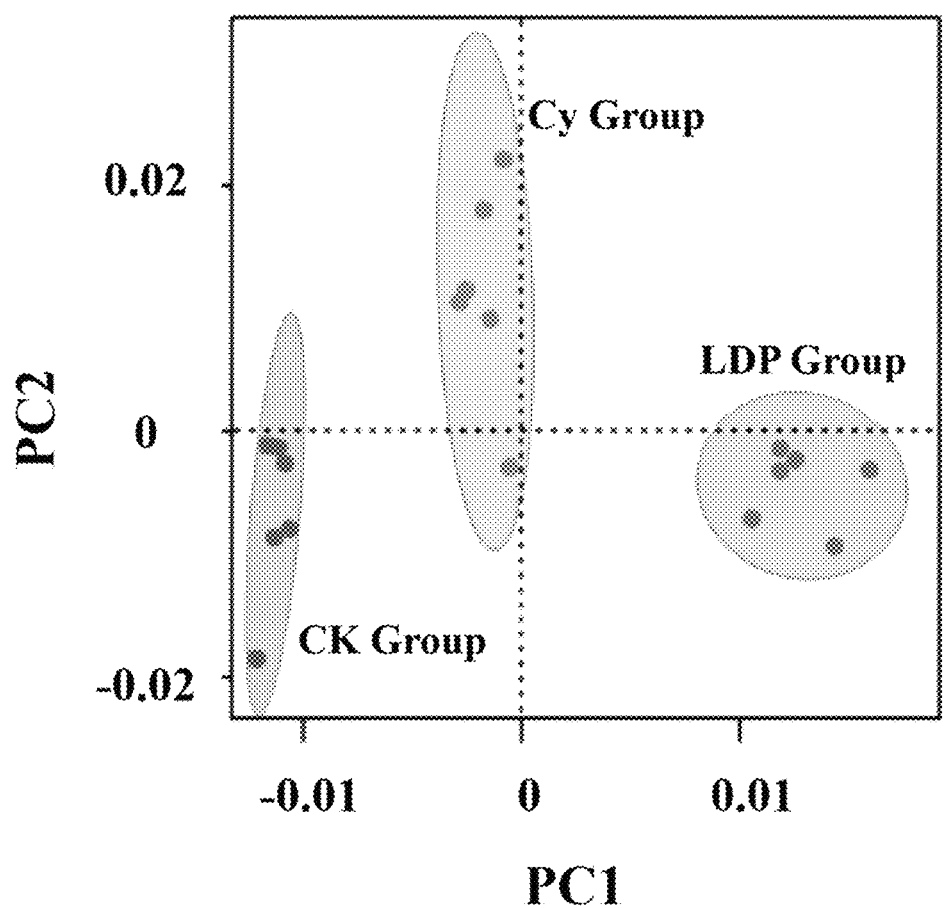
FIG. 12 illustrates a principal component analysis (PCA) analysis at OTU level.
Figure 13:
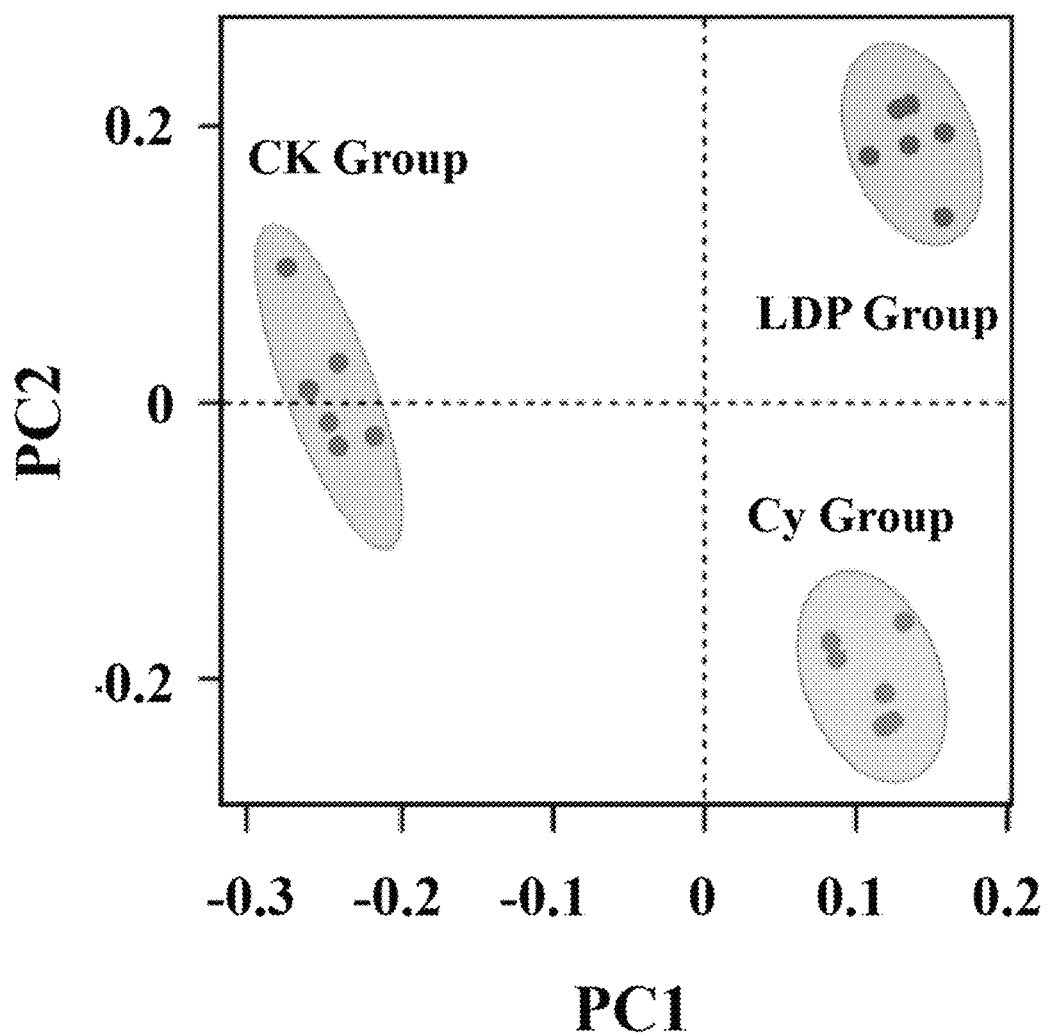
FIG. 13 illustrates a principal co-ordinates analysis (POCA) at OTU level.
Figure 14:
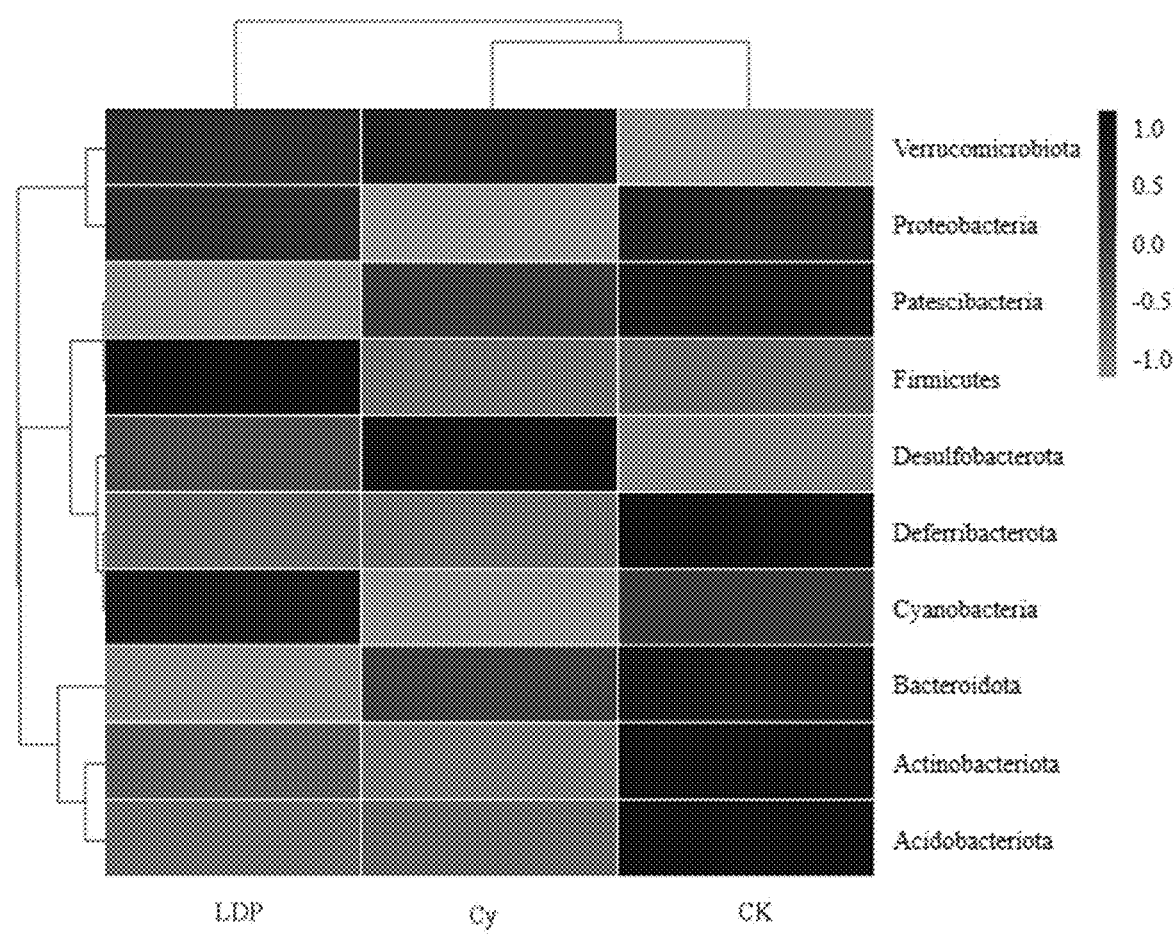
FIG. 14 is a community column diagram of horizontal community composition analysis of mouse intestines at phylum level.
Figure 15:
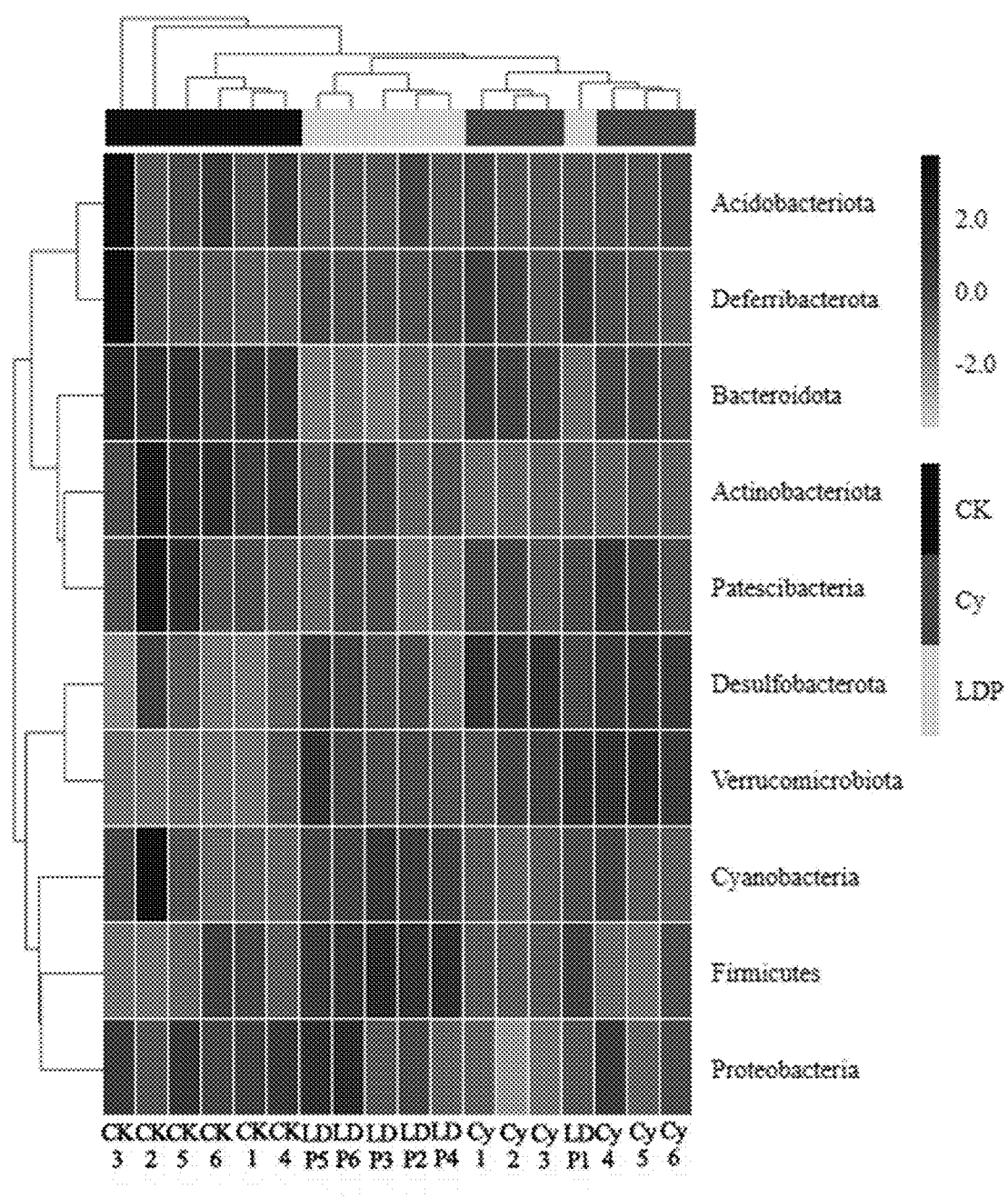
FIG. 15 is a community heat map of horizontal community composition analysis of mouse intestines at phylum level.

2.7 Microbial Diversity

α-diversity analysis (FIG. 11A-FIG. 11D) show that the *Lyophyllum decastes* polysaccharide can enhance the abundance and uniformity of microbial community. Chao 1 index, ACE index and Shannon index of Cy group are lower than those of CK group. Compared with Cy group, the index of *Lyophyllum decastes* polysaccharide group is higher, closer to that of CK group, and Simpson index shows a opposite trend. β-diversity analysis suggests (FIGS. 12-13) that there is no crossover of microbial community between Cy group and CK group, indicating that there is a big difference between the two groups, and the microbial community structure of *Lyophyllum decastes* polysaccharide group is closer to that of CK group. The microbial community composition is classified and analyzed in detail at the phylum level, and it is found that Cy treatment may increase the abundance of Verrucomicrobia and decrease the abundance of Firmicutes and Bacteroidetes, while the *Lyophyllum decastes* polysaccharide can reverse these changes, so that the abundance of Verrucomicrobia is decreased and the abundance of Firmicutes is increased (FIGS. 14-15).

The above-mentioned embodiments only describe the preferred mode of the present disclosure, and do not limit the scope of the present disclosure. Under the premise of not departing from the design spirit of the present disclosure, various modifications and improvements made by ordinary technicians in the field to the technical scheme of the present disclosure shall fall within the protection scope determined by the claims of the present disclosure.

What is claimed is:

1. A preparation method of a *Lyophyllum decastes* polysaccharide, comprising following steps:
   (1) adding an aqueous solution containing EDTA-2Na into a fruiting body of *Lyophyllum decastes*, performing ultrasonic treatment, and then performing water extraction treatment to obtain an extractive solution;
   (2) concentrating the extractive solution, adding anhydrous ethanol for precipitation, followed by centrifuging to obtain precipitates, then obtaining a crude *Lyophyllum decastes* polysaccharide; and
   (3) conducting removal of proteins and dialysis of the crude *Lyophyllum decastes* polysaccharide to obtain the *Lyophyllum decastes* polysaccharide;
   wherein in step (1), a concentration of the EDTA-2Na in the aqueous solution containing EDTA-2Na is 1 wt %; a material-liquid ratio of the fruiting body of the *Lyophyllum decastes* to the aqueous solution containing EDTA-2Na is 1 g:22 mL; a duration of the ultrasonic treatment is 30 min; a power of the ultrasonic treatment is 100 W; and a temperature of the water extraction treatment is 98° C.

* * * * *